(12) United States Patent
Bhaskaran et al.

(10) Patent No.: US 10,493,088 B2
(45) Date of Patent: Dec. 3, 2019

(54) COMPOSITION OF TRIGOFOENOSIDE AND FLAVONOIDS AND METHODS THEREOF

(71) Applicant: Indus Biotech Private Limited, Pune (IN)

(72) Inventors: Sunil Bhaskaran, Pune (IN); Mohan Vishwaraman, Pune (IN)

(73) Assignee: Indus Biotech Private Limited, Pune (IN)

( * ) Notice: Subject to any disclaimer, the term of this patent is extended or adjusted under 35 U.S.C. 154(b) by 0 days.

(21) Appl. No.: 15/760,798

(22) PCT Filed: Sep. 17, 2016

(86) PCT No.: PCT/IB2016/055565
§ 371 (c)(1),
(2) Date: Mar. 16, 2018

(87) PCT Pub. No.: WO2017/046777
PCT Pub. Date: Mar. 23, 2017

(65) Prior Publication Data
US 2018/0256621 A1    Sep. 13, 2018

(30) Foreign Application Priority Data
Sep. 19, 2015  (IN) ............................ 918/MUM/2015

(51) Int. Cl.
| A61K 31/7048 | (2006.01) |
| A61K 9/00 | (2006.01) |
| A61P 9/12 | (2006.01) |
| A61P 11/00 | (2006.01) |
| A61K 36/48 | (2006.01) |

(52) U.S. Cl.
CPC ........ *A61K 31/7048* (2013.01); *A61K 9/0073* (2013.01); *A61K 36/48* (2013.01); *A61K 2236/00* (2013.01); *A61K 2236/35* (2013.01); *A61K 2236/39* (2013.01); *A61K 2236/51* (2013.01); *A61K 2300/00* (2013.01); *A61P 9/12* (2018.01); *A61P 11/00* (2018.01)

(58) Field of Classification Search
CPC ......... A61K 31/7048; A61P 9/12; A61P 11/00
See application file for complete search history.

(56) References Cited

U.S. PATENT DOCUMENTS

| 8,633,229 B2 | 1/2014 | Bhaskaran et al. |
| 2005/0233014 A1 | 10/2005 | Lee et al. |
| 2012/0282332 A1 | 11/2012 | Bhaskaran et al. |

FOREIGN PATENT DOCUMENTS

| CN | 102920727 A | 2/2013 |
| CN | 103304605 A | 9/2013 |
| CN | 103923074 A | 7/2014 |
| WO | 2008107909 A1 | 9/2008 |
| WO | 2009121155 A2 | 10/2009 |
| WO | 2009136219 A1 | 11/2009 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Mayo Clinic entry for pulmonary fibrosis, https://www.mayoclinic.org, accessed online on Apr. 9, 2019. (Year: 2019).*
Mayo Clinic entry for pulmonary hypertension, https://www.mayoclinic.org, accessed online on Apr. 9, 2019. (Year: 2019).*
Kadhare et al., "Acute and repeated doses (28 days) oral toxicity study of glycosides based standardized fenugreek seed extract in laboratory mice", Regulatory Toxicology and Pharmacology, 2015, pp. 323-334.
Kandhare et al., "Effect of glycosides based standardized fenugreek seed extract in bleomycin-induced pulmonary fibrosis in rats: Decisive role of Bax, Nrf2, NF-kB, Muc5ac, TNF-a and IL-1B", Chemico-Biological Interactions, 2015, pp. 151-165, vol. 237.
Murugesan et al., "Cardioprotective effect of fenugreek on isoproterenol-induced myocardial infarction in rats", Indian J Pharmacol., 2011, pp. 516-519, vol. 43:5.
TKDL Abstract No. VK6/121 "Mahadraksadi Cumam" Rasayogaratnckara—Translated by Pammi Satyanarayana Sastry, Edited by Koppula Hemadri, 1st Edition, 2005, Dr Achanta Lakshmipathi Ayurveda Library Trust, 2—Geeta Apartments New Ayodhyanagar (Vijayawada), pp. 201-202.
TKDL Abstract No. VKI/605 A "Mahadraksadi Cuma" Basavarcjoyam-Chaukhambha Sanskrit Pratishan, Delhi; Edition. 1st Reprint; 2005 [Time oforigin 15th century], pp. 240.
Yacoubi et al., "Anti-oxidative and anti-inflammatory effects of Trigonella foenum-graecum Linnaeus, 1753 (Fenugreek) seed extract in experimental pulmonary fibrosis", Journal of Medicinal Plants Research, 2011, pp. 4315-4325, vol. 5:17.

* cited by examiner

*Primary Examiner* — Jonathan S Lau
(74) *Attorney, Agent, or Firm* — The Webb Law Firm

(57) ABSTRACT

The present disclosure relates to composition comprising Trigofoenoside, Vitexin, Iso-vitexin, Vitexin-2-o-rhamnoside Vicenin-1 and fiber, optionally along with pharmaceutically acceptable excipient(s) and method(s) of preparing said composition. The present disclosure also relates to methods of treating various conditions such as, but not limited to, Hypoxia, ulmonary Hypertension, Pulmonary Fibrosis and Sinusitis using the said composition.

19 Claims, 10 Drawing Sheets

COMPOSITION OF TRIGOFOENOSIDE AND FLAVONOIDS AND METHODS THEREOF

CROSS-REFERENCE TO RELATED APPLICATIONS

This application is the United States national phase of International Application No. PCT/IB2016/055565 filed Sep. 17, 2016, and claims priority to Indian Patent Application No. 918/MUM/2015 filed Sep. 19, 2015, the disclosures of which are hereby incorporated in their entirety by reference.

TECHNICAL FIELD

The present disclosure broadly relates to the field of phytochemistry, biotechnology and biochemistry. Specifically, the present disclosure relates to a composition comprising Trigofoenoside, Vitexin, Iso-vitexin, Vitexin-2-o-rhamnoside, Vicenin-1 and fiber, optionally along with pharmaceutically acceptable excipient; and methods of preparing said composition. The present disclosure also relates to method of managing various conditions such as hypoxia, pulmonary hypertension, pulmonary fibrosis and sinusitis using the said composition.

BACKGROUND AND PRIOR ART

Being rich in phytochemicals, Fenugreek (*Trigonella foenum-graecum*) has traditionally been used as food, forage and medicinal plant. Fenugreek has a long history of medical uses in Ayurvedic and Chinese medicine, and has been used for numerous indications, including labor induction, aiding digestion, and as a general tonic to improve metabolism and health.

Fenugreek is rich in its chemical constituents. Fenugreek seed contains about 45-60% carbohydrates, mainly mucilaginous fiber (galactomannans); proteins which are high in lysine and tryptophan; fixed oils such as lipids; pyridine-type alkaloids, mainly trigonelline, choline, gentianine, and carpaine; flavonoids such as apigenin, luteolin, orientin, quercetin, vitexin, and isovitexin; free amino acids such as 4-hydroxyisoleucine, arginine, histidine, and lysine; calcium and iron; saponins, like glycosides which yield steroidal sapogenins on hydrolysis (such as diosgenin, yamogenin, tigogenin, neotigogenin); cholesterol and sitosterol; vitamins A, B1, C, and nicotinic acid; volatile oils such as n-alkanes and sesquiterpenes; and sugars such as raffinose, stachyose, sucrose, fructose, mannose, verbascose and xylose. The seeds also contain saponin fenugrin B and coumarin compounds. The seed is also responsible for about 8% of fixed, foul-smelling oil. Several C-glycoside flavones have also been identified in the seeds of fenugreek. These include vitexin, vitexin glycoside, and an arabinoside of orietin (iso-orientin), minor steroidal sapogenins (fenugreekine, smilagenin, sarsasapogenin, yuccagenin), and up to 50% of mucilaginous fiber.

These different chemical constituents have shown diverse therapeutic effects. The component called fenugreekine, a steroidal sapogenin peptide ester has hypoglycemic properties and has shown improved pancreatic function. It helps to delay gastric emptying, slow carbohydrate absorption, and inhibit glucose transport in humans. Trigonelline is suggested to exert hypoglycemic effects in healthy patients without diabetes. The steroidal saponins (diosgenin, yamogenin, tigogenin and neotigogenin) are thought to inhibit cholesterol absorption and synthesis and hence its potential role in arteriosclerosis. It is also used topically to treat inflammation, and to promote postpartum lactation in animals. At present, diosgenin, a steroid sapogenin, is used in the manufacture of birth control pills. Plant phenolics have potential health benefits mainly due to their antioxidant properties such as reactive oxygen species (ROS) scavenging and inhibition, electrophile scavenging and metal chelation. They have also been reported to exhibit pharmacological properties such as antitumor, antiviral, antimicrobial, anti-inflammatory, hypotensive and antioxidant activity.

Thus, fenugreek is researched for different chemical constituents and therapeutic activities. Fenugreek is reported as a cultivated crop in various parts of Europe such as in Austria, France, Germany, Greece, Portugal, Russia, Spain, Switzerland, Turkey and United Kingdom (UK); Northern Africa such as in Egypt, Ethiopia, Kenya, Morocco, Sudan, Tanzania and Tunisia; West and South Asia such as in China, India, Iran, Israel, Japan, Lebanon and Pakistan; North and South America and Australia.

Plant growth and distribution are limited by environmental factors. The environmental aspects that affect plant growth and phyto-chemical distribution are light, temperature, water (humidity), and nutrition. These environmental conditions are different in different geographical locations throughout the world. They have shown prominent effect on plant growth, chemical distribution in terms of quality and quantity of active principles and on genetic diversity as well.

However, due to ever-growing needs of the developing population, there is a need to identify and isolate specific components available in biological sources such as Fenugreek, for several applications.

Oxygen is essential for life. Carbohydrates and fatty acids are the most important fuels for generating ATP in animal cells. Respiration in animal cells depends on oxygen. Electrons from the chemical bonds of the fuel source combine with oxygen and hydrogen ions to form water and carbon dioxide. Cells couple this reaction to the production of ATP. High-energy phosphate in the form of ATP is required for many synthetic and degradative processes within the cell. These include membrane transport, protein synthesis, lipogenesis, and the deacylation-reacylation reactions necessary for phospholipid turnover. The body functioning gets affected because of low levels of oxygen in the blood and air. Ultimately this reduced air and blood flow affects oxygen transportation through the lungs. The impaired levels of oxygen in lungs results in high pressure on arteries and veins leading to scarring of tissues and abnormal arterial and venous blood pressures.

With prolonged or increased depletion of ATP, structural disruption of the protein synthetic apparatus occurs, resulting in detachment of ribosomes from the rough endoplasmic reticulum and dissociation of polysomes into monosomes, with a consequent reduction in protein synthesis. Ultimately, there is irreversible damage to mitochondrial and lysosomal membranes, and the cell undergoes necrosis.

Hypoxia, is a pathological condition in which the body or a region of the body is deprived of an adequate oxygen supply. When oxygen levels are low for a long time, pulmonary arteries constrict and their walls become thickened. This constriction and thickening increase the pressure in the pulmonary arteries. Lung disorders that damage or decrease the amount of lung tissue (for example, emphysema) also decrease the number of blood vessels in the lungs. The decreased number of blood vessels increases pressure in the remaining vessels leading to pulmonary hypertension.

Pulmonary hypertension (PAH) is a rare lung disorder in which the blood pressure in the pulmonary artery rises far above normal levels and may become life threatening. It is characterized by vascular remodelling of the distal pulmonary arterial circulation. The remodelling seen in PAH includes both apoptosis and proliferation of pulmonary vascular endothelial cells, deposition of extracellular matrix proteins, and perivascular inflammation.

Increased pulmonary venous pressure is typically caused by disorders that affect the left side of the heart and raise left chamber pressures, which ultimately lead to elevated pressure in the pulmonary veins. Elevated pulmonary venous pressures can cause acute damage to the alveolar-capillary wall and subsequent edema. Persistently high pressures may eventually lead to irreversible thickening of the walls of the alveolar-capillary membrane, decreasing lung diffusion capacity. In most patients, pulmonary hypertension eventually leads to right ventricular hypertrophy followed by dilation and right ventricular failure. Right ventricular failure limits cardiac output during exertion.

Pulmonary fibrosis (PF) refers to scarring in the lungs. Pulmonary fibrosis is associated with pulmonary vascular remodelling, fostering the development of pulmonary hypertension. It describes a group of lung diseases in which thickening of the walls of the air sacs (called alveoli), caused by scarring the tissue, makes it hard for oxygen to get into the blood. Low oxygen levels (and the stiff scar tissue itself) can cause shortness of breath, particularly when walking and exercising. Pulmonary fibrosis can be caused by an identifiable irritation to the lungs, but in many cases the cause is unknown.

Hypersecretion of airway mucus leads via impairment of the muco-ciliary clearance and bacterial superinfection to respiratory failure. The major components of the mucus matrix forming family of mucins in the airways are MUC5AC and MUC5B. The major components of mucus are large, heavily glycosylated proteins (mucins) that provide airway secretions with their characteristic viscosity, adhesiveness, and elasticity.

Reactive oxygen species (ROS) released from activated neutrophils cause mucin Muc5ac synthesis via transactivation of epidermal growth factor receptor in a human pulmonary mucoepidermoid cell line. Furthermore, neutrophil elastase induces the overexpression of Muc5ac in cultured human bronchial epithelial cells by an oxidant-dependent mechanism. In sinusitis, the mucin formed by Muc5ac genes gets clogged in upper respiratory tract where chick bones and forehead get affected by mucus secretion.

In acute sinusitis, the infection develops quickly (over a few days) and lasts a short time. Many cases of acute sinusitis last a week or so but it is not unusual for it to last 2-3 weeks (that is, longer than most colds). Sometimes it lasts longer. Sinusitis is said to be acute if it lasts from 4-30 days and subacute if it lasts 4-12 weeks. However, in chronic sinusitis, a sinusitis becomes persistent and lasts for longer than 12 weeks.

Current Therapy

Current therapies for PAH include pharmacologic agents that 1) inhibit PDE5, 2) antagonize endothelin, or 3) supplement the prostaglandin pathway with exogenous prostacyclins. These treatments improve longevity and performance of activities of daily life for PAH patients, but do not halt the ongoing cytoproliferative process that inexorably modifies pulmonary vascular architecture, and leads to lung transplant.

Pulmonary rehabilitation—Pulmonary rehabilitation is a structured exercise program for people with chronic lung diseases, including PF and hypoxia, with the goal of restoring a patient's ability to function without extreme breathlessness. Typically, pulmonary rehabilitation will include conditioning; exercise training and breathing exercises; anxiety, stress, and emotional management; nutritional counseling; education; and other components.

Lung Transplantation—Pulmonary fibrosis is now the leading indication for lung transplantation in the United States; in 2013, PF accounted for nearly half of all lung transplants performed. Transplantation can improve both longevity and quality of life in patients who have no other significant health problems.

N-acetylcysteine (NAC): NAC is a naturally occurring anti-oxidant. In the past, it was thought that NAC could help protect the lung from "oxidative injury" that occurs in some forms of PF. In 2014, a clinical trial found that NAC did not have a substantial beneficial impact in Idiopathic Pulmonary Fibrosis (IPF).

Nintedanib (Ofev®): Nintedanib is an anti-fibrotic drug that is approved to treat IPF in the United States. In clinical trials, nintedanib has been shown to slow the decline in lung function in mild-to-moderate IPF. It is taken by mouth twice a day.

These treatments improve longevity and performance of activities of daily life of PF patients, but do not halt scarring of the lung tissues that affect the air sacs and airways leading to ILD or PF and lung transplant.

There are over-the-counter medicines for sinusitis such as Paracetamol and ibuprofen for relieving pain and fever; decongestants and saline nasal sprays or drops for relieving a blocked nose. These drugs provide instant relief but fail to cease the mucous formation in upper respiratory tract. There is need to develop a drug which would able to prevent disease progression by way of stopping mucous formation and clogging of nose leading to sinusitis.

Prior Art:

CN103304605 A discloses a method for preparing a flavonoid glycoside and stilbene glucoside type compound from fenugreek by virtue of a high speed counter-current chromatography (HSCCC) separation technology, so that the separation time is effectively shortened, and the shortcomings of complicated operation, sample dis adsorption loss, low yield, etc., of conventional preparation methods are overcome. According to the method, the technology is simple, the reproducibility is high, the separation efficiency is high; and the obtained monomer content is higher than 96.0 percent. The document revolves around efficient process to obtain glycosides and glucosides.

WO 2009121155 A2 discloses benzopyranone compounds of formula (I) in the manufacture of a medicament that is useful in the treatment of diseases, dysfunctions and disturbances associated with monoamine oxidase, such as depression and diseases related to depression, phobias, attention deficit, drug abuse, behavioral maladjustment, Parkinson's disease, Alzheimer's disease and migraine. In an even more particular embodiment, the disease includes major depression or depressant symptoms that do not respond to conventional treatment with other antidepressants.

CN 103923074 A discloses a method for extracting vitexin and trigonelline from fenugreek. The method comprises various steps of obtaining vitexin and trigonelline containing water extract with the yield of 20%-35%, from a certain quantity of fenugreek seeds and fenugreek leaves. The process results in increased extraction rate of vitexin and trigonelline and also improves the extraction purity of vitexin and trigonelline. Thus, the document mainly focuses on obtaining purer form of trigonelline and vitexin by a patented process.

CN 102920727 A provides a method for preparing extracts rich in vitexin rhamnoside and vitexin glucoside, and relates to the field of herbal extracting of hawthorn leaves. According to the method, vitexin rhamnoside constitutes 30%-55% of the extract while vitexin glucoside constitutes 10%-35% of the extract. The document focuses on obtaining two ingredients of high purity.

Lamia Yacoubi et al (September, 2011) examines fenugreek (*Trigonella foenum-graecum* Linnaeus), and its phenolylic extract for inhibition of bleomycin induced lung fibrosis in rats. No correlation is found with increasing fibrosis, suggesting that a direct role for inflammation in pulmonary fibrosis is unlikely. The data suggests, in the first hand, that fenugreek's polyphenol has a potent antioxidant activity and therefore has a potent anti-inflammatory activity against bleomycin induced lung fibrosis model in rats, and in the second hand, they confirm that besides inflammation, other factors probably interfere in the pathogenesis of pulmonary fibrosis.

Madhesh Murugesan et al (September, 2011) reveals that administration of fenugreek is more effective in reducing the extent of myocardial damage and significantly counteracted the oxidative stress during isoproterenol induced myocardial infarction in rats.

However, none of the prior arts either alone or in combination teach a composition for use in treating conditions where oxygen levels are reduced less than normal and thereby causing impairment of oxygen in lungs leading to diseases such as hypoxia, pulmonary hypertension, pulmonary fibrosis and sinusitis. There is a need to develop a safe and efficacious regime which would not only cease disease progression but also provide a protection to the organs from being damaged to a stage of transplantation.

Hence, the present disclosure overcomes the various drawbacks observed in the prior art and provides methods for arriving at composition with specific active components from sources such as, but not limited to Fenugreek, and removing all other active principles such as amino acids, alkaloids, saponins, etc. The composition of the present disclosure is effective in managing conditions such as, but not limited to, hypoxia, pulmonary hypertension, pulmonary fibrosis and sinusitis.

STATEMENT OF THE DISCLOSURE

Accordingly, the present disclosure relates to a composition comprising Trigofoenoside, Vitexin, Iso-vitexin, Vitexin-2-o-rhamnoside, Vicenin-1 and fiber, optionally along with pharmaceutically acceptable excipient; a method for obtaining composition comprising Trigofoenoside, Vitexin, Iso-vitexin, Vitexin-2-o-rhamnoside, Vicenin-1 and fiber, optionally along with pharmaceutically acceptable excipient, said method comprising acts of: (a) extracting flaked source material of the composition with first solvent to obtain first extract, (b) treating the first extract with a second solvent to obtain second extract, (c) re-extracting the second extract with a third solvent to obtain a clear extract, (d) concentrating the clear extract to obtain solid mass, (e) dissolving the solid mass in aqueous solvent to obtain clear solution, (f) regenerating and washing adsorbent with solvent to obtain regenerated and washed adsorbent, (g) passing the clear solution through the regenerated and washed adsorbent, re-washing the adsorbent with solvent and eluting with an alcoholic solvent to obtain an elute, and (h) concentrating the elute and optionally adding pharmaceutically acceptable excipient to obtain the composition; and a method of managing a disease selected from group comprising hypoxia, pulmonary hypertension, pulmonary fibrosis and sinusitis, or any combinations thereof, said method comprising act of administering composition comprising Trigofoenoside, Vitexin, Iso-vitexin, Vitexin-2-o-rhamnoside, Vicenin-1 and fiber, optionally along with pharmaceutically acceptable excipient to subject in need thereof.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, in accordance with the present disclosure where:

FIGS. 1*a* and 1*b* are HPLC graphs depicting the presence of Trigofoenoside, Vitexin, Iso-vitexin, Vitexin-2-o-rhamnoside, Vicenin-1 in the instant composition, according to one embodiment.

FIG. 2*a* depicts HPLC graph of standard Trigofoenoside; FIG. 2*b* depicts HPLC graph of standard Vicenin-1; FIG. 2*c* depicts HPLC graph of standard Vitexin-2-o-rhamnoside; FIG. 2*d* depicts HPLC graph of standard Vitexin; and FIG. 2*e* depicts HPLC graph of standard Iso-vitexin.

Figure 6A:
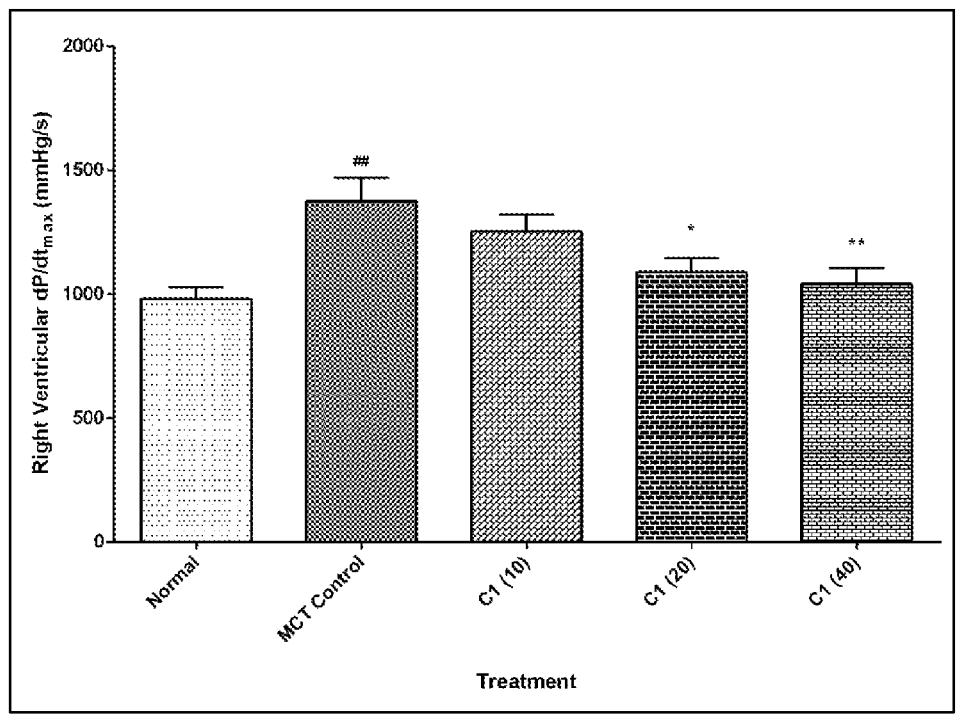
Figure 6B:
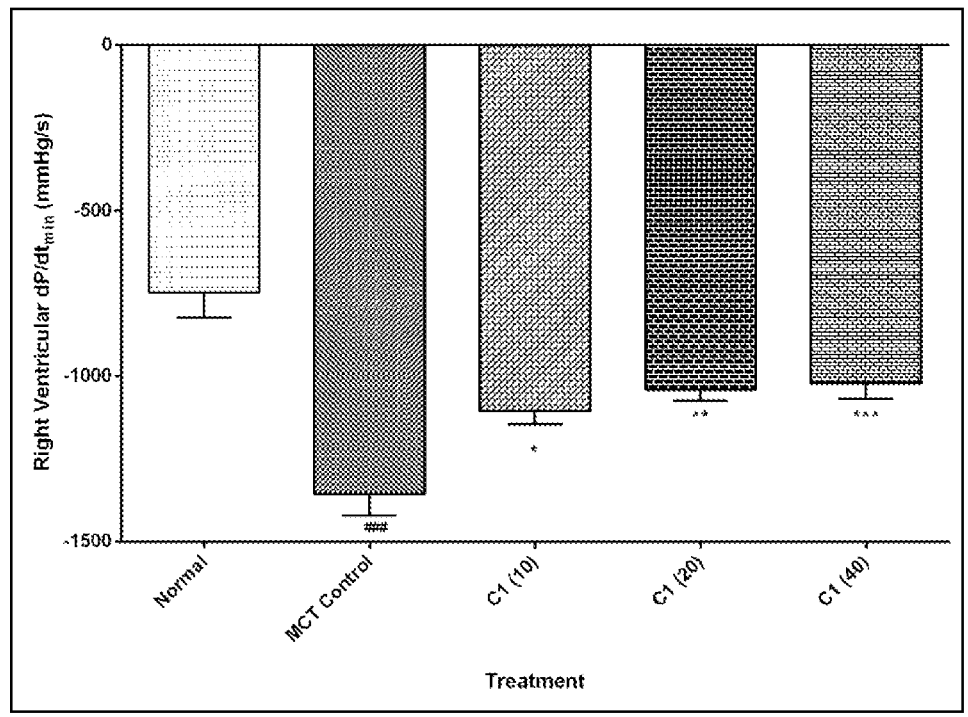

FIG. 6*a* is a bar graph depicting the effect of the instant composition on MCT induced alteration in right ventricular $dP/dt_{min}$; and FIG. 6*b* is a bar graph depicting the effect of the instant composition on MCT induced alteration in right ventricular $dP/dt_{max}$, according to one embodiment.

Figure 7A:
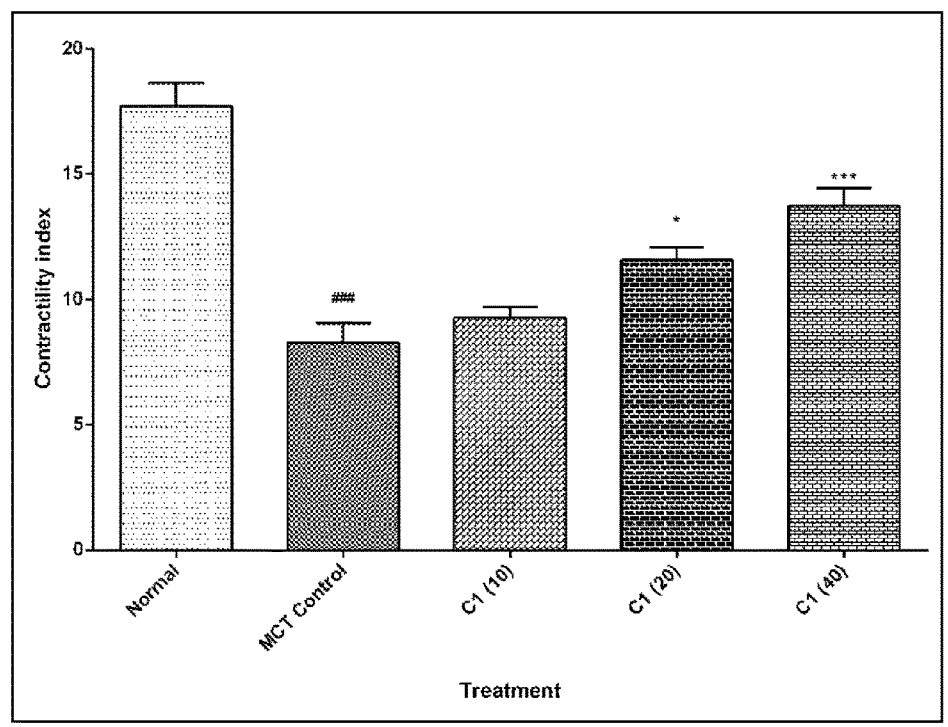
Figure 7B:
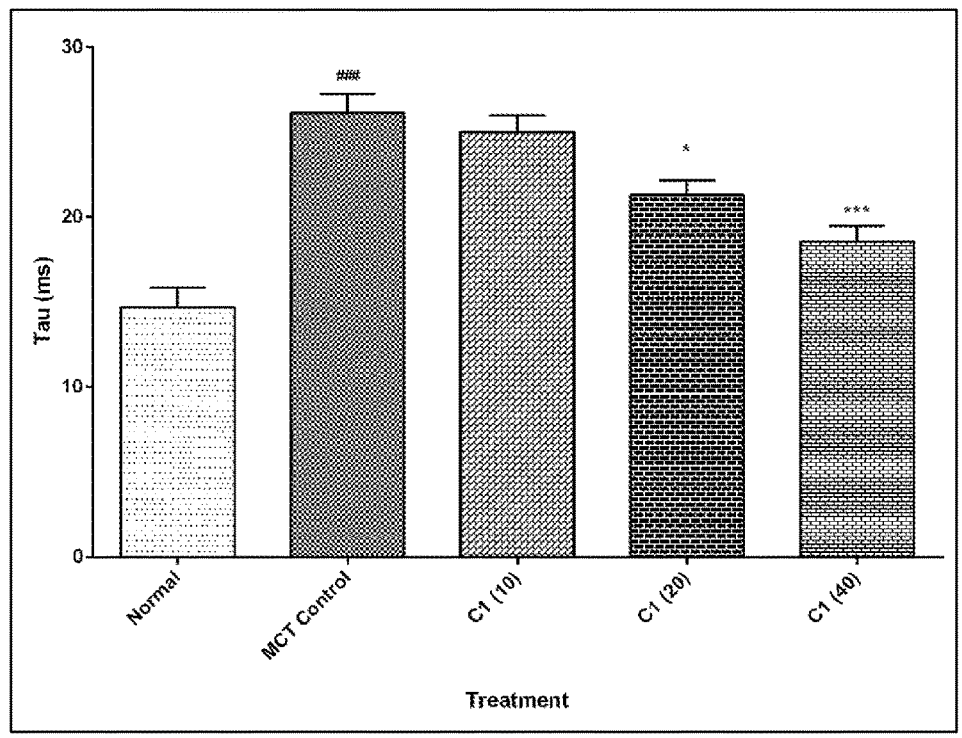

FIG. 7*a* is a bar graph depicting the effect of the instant composition on MCT induced alteration in contractility index, and FIG. 7*b* is a bar graph depicting the effect of the instant composition on MCT induced alteration in tau, according to one embodiment.

Figure 8:
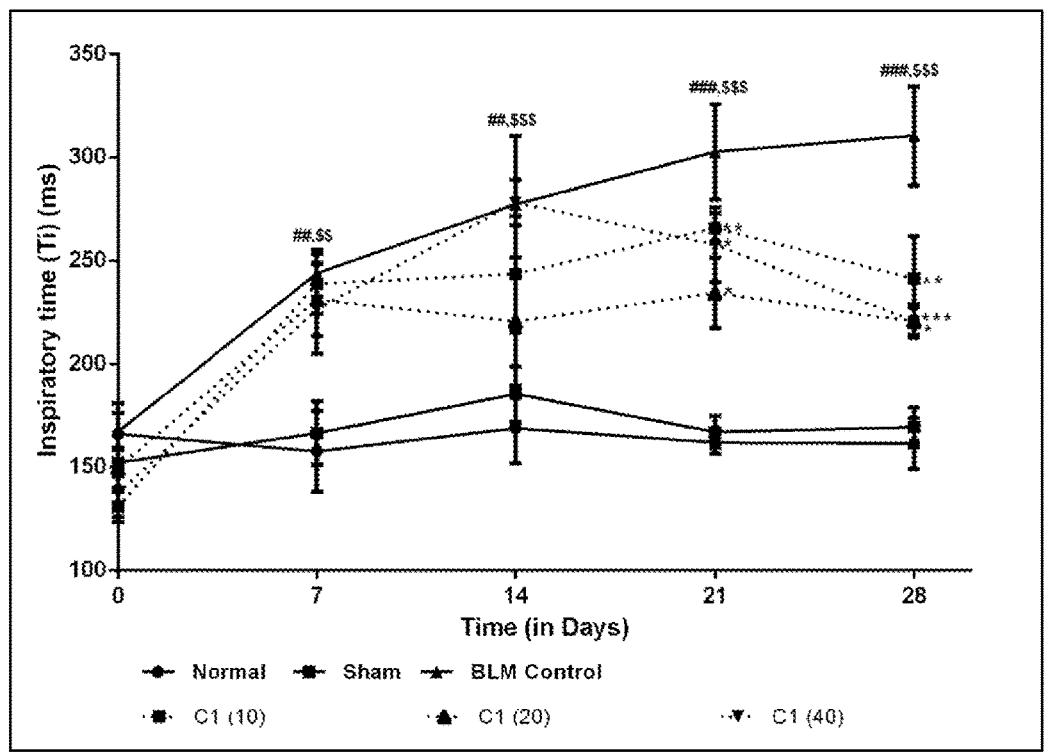

FIG. 8 is a graph depicting the effect of the instant composition on bleomycin induced alteration in inspiratory time (Ti), according to one embodiment.

Figure 9:
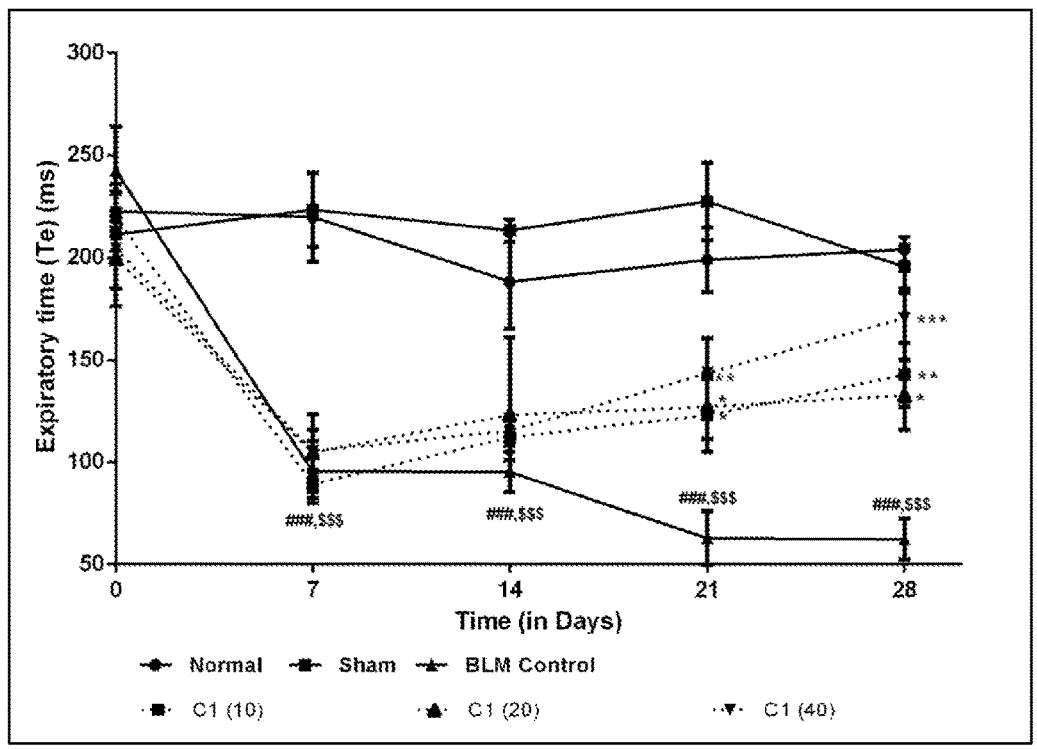

FIG. 9 is a graph depicting the effect of the instant composition on bleomycin induced alteration in expiratory time (Te), according to one embodiment.

Figure 10:
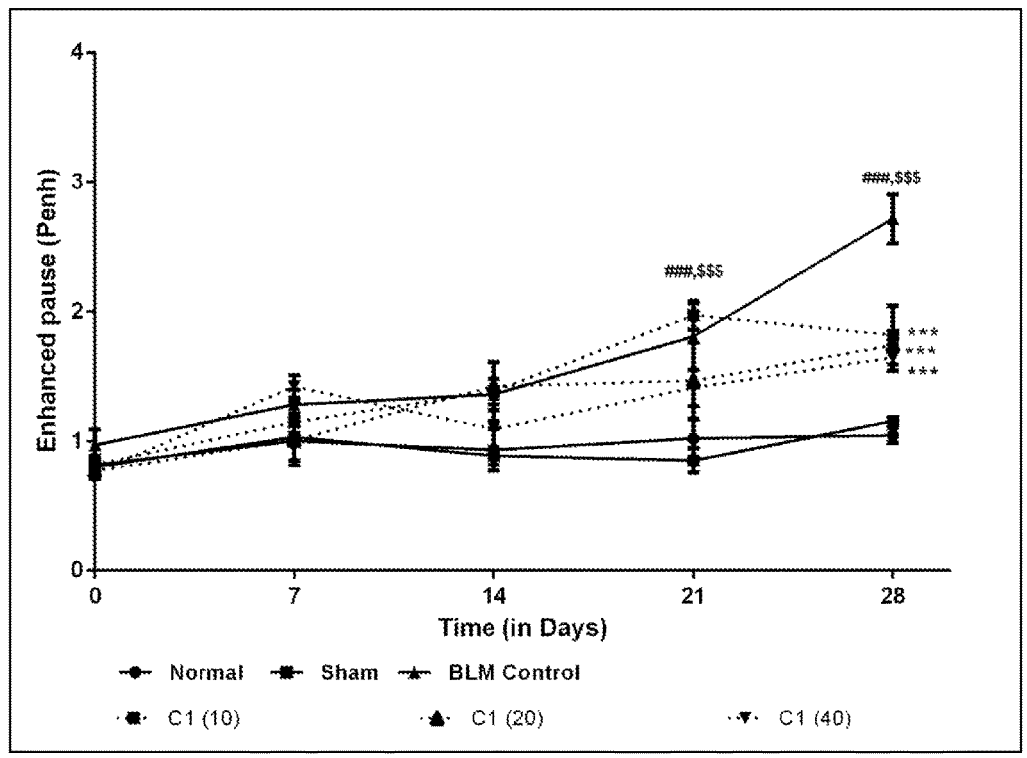

FIG. 10 is a graph depicting the effect of the instant composition on bleomycin induced alteration in enhanced pause ($P_{enh}$), according to one embodiment.

Figure 11:
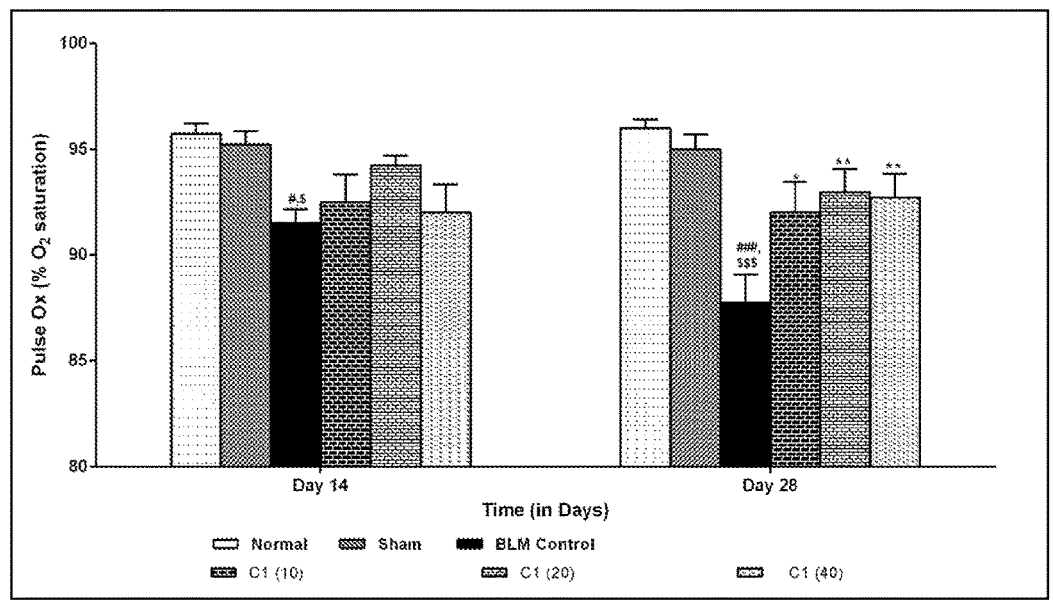

FIG. 11 is a bar graph depicting the effect of the instant composition on bleomycin induced alteration in peripheral blood oxygen content (pulse Ox), according to one embodiment.

Figure 12:
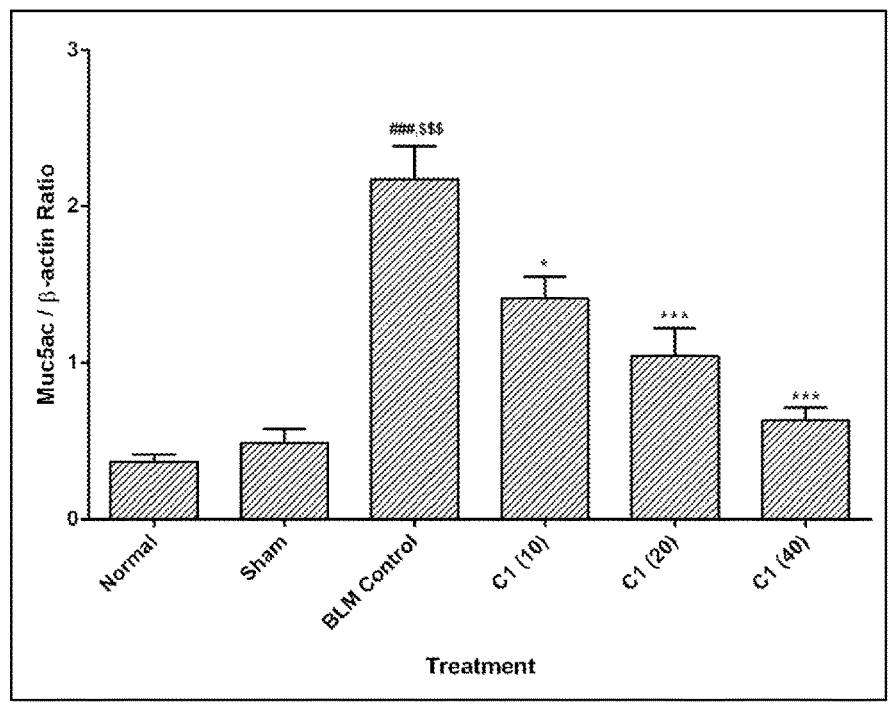

FIG. 12 is a bar graph depicting the effect of the instant composition on bleomycin induced alteration in Muc5ac m-RNA expression in lung, according to one embodiment.

Figure 13:
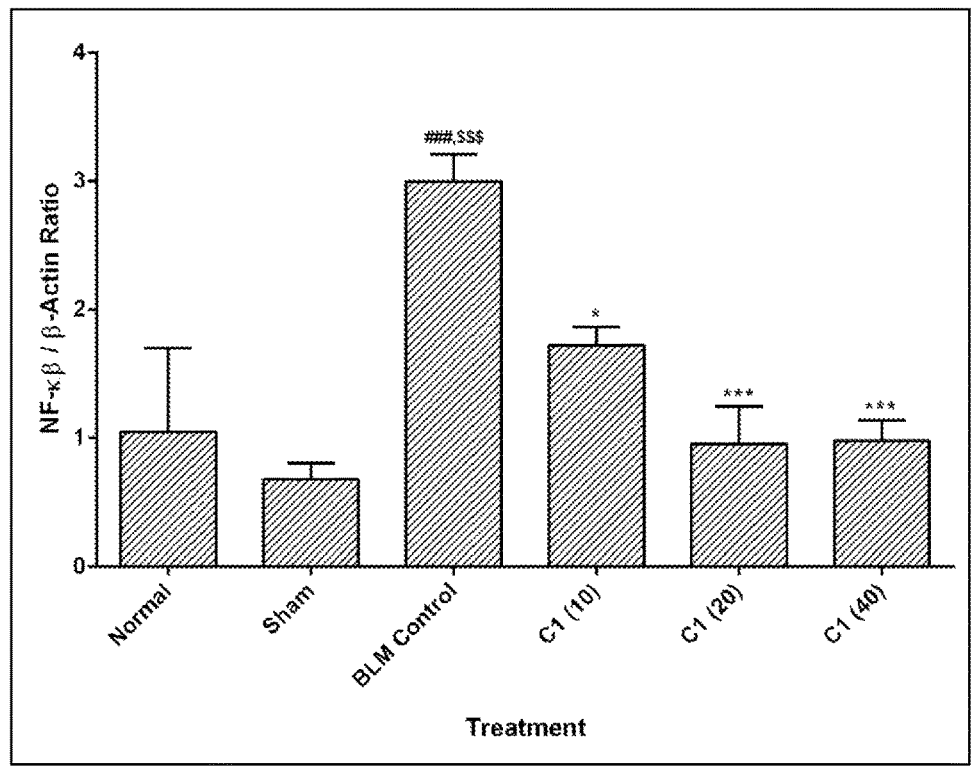

FIG. 13 is a bar graph depicting the effect of the instant composition on bleomycin induced alteration in NF-kB m-RNA expression in lung, according to one embodiment.

DETAILED DESCRIPTION OF THE DISCLOSURE

The present disclosure relates to a composition comprising Trigofoenoside, Vitexin, Iso-vitexin, Vitexin-2-o-rhamnoside, Vicenin-1 and fiber, optionally along with pharmaceutically acceptable excipient.

The present disclosure also relates to a method for obtaining composition comprising Trigofoenoside, Vitexin, Iso-vitexin, Vitexin-2-o-rhamnoside, Vicenin-1 and fiber, optionally along with pharmaceutically acceptable excipient, said method comprising acts of:
a) extracting flaked source material of the composition with first solvent to obtain first extract;
b) treating the first extract with a second solvent to obtain second extract;
c) re-extracting the second extract with a third solvent to obtain a clear extract;
d) concentrating the clear extract to obtain solid mass;
e) dissolving the solid mass in aqueous solvent to obtain clear solution;
f) regenerating and washing adsorbent with solvent to obtain regenerated and washed adsorbent;
g) passing the clear solution through the regenerated and washed adsorbent, re-washing the adsorbent with solvent and eluting with an alcoholic solvent to obtain an elute; and
h) concentrating the elute and optionally adding pharmaceutically acceptable excipient to obtain the composition.

In an embodiment of the present disclosure, said source material is from a plant source, preferably *Trigonella foenum graecum*.

In another embodiment of the present disclosure, the extracting with the first solvent is carried out at temperature ranging from about 25° C. to about 30° C., preferably about 25° C. to about 27° C., at time period of about 3.8 hours to about 4.2 hours, preferably about 4 hours; and said first solvent is an aliphatic compound selected from group comprising n-Hexane, n-Pentane and n-Heptane, preferably n-Hexane.

In yet another embodiment of the present disclosure, the treating with the second solvent is carried out at temperature ranging from about 26° C. to about 30° C., preferably about 27° C. to about 29° C.; and said second solvent is ethyl acetate.

In yet another embodiment of the present disclosure, the extracting with the third solvent is carried out in counter-current manner at temperature ranging from about 22° C. to about 27° C., preferably about 22° C. to about 25° C., at time period ranging from about 7 hours to about 9 hours, preferably about 8 hours; and said third solvent is n-Butanol.

In yet another embodiment of the present disclosure, the concentrating is carried out by vacuum concentration.

In yet another embodiment of the present disclosure, said aqueous solvent is deionized water.

In still another embodiment of the present disclosure, said adsorbent is a resin bed, preferably Amberlite XAD-16; wherein the solvent for washing the adsorbent is selected from group comprising isopropyl alcohol, ethanol and deionized water, or any combinations thereof; wherein the solvent for re-washing the adsorbent is selected from group comprising sodium chloride saline and water, or a combination thereof; and wherein said alcoholic solvent is selected from group comprising ethanol and isopropyl alcohol, preferably isopropyl alcohol.

The present disclosure further relates to a method of managing a disease selected from group comprising hypoxia, pulmonary hypertension, pulmonary fibrosis and sinusitis, or any combinations thereof, said method comprising act of administering composition comprising Trigofoenoside, Vitexin, Iso-vitexin, Vitexin-2-o-rhamnoside, Vicenin-1 and fiber, optionally along with pharmaceutically acceptable excipient to subject in need thereof.

In an embodiment of the present disclosure, the Trigofoenoside, the Vitexin, the Iso-vitexin, the Vitexin-2-o-rhamnoside and the Vicenin-1, together have concentration ranging from about 8% w/w to about 31% w/w; the fiber is present at concentration ranging from about 69% w/w to about 92% w/w.

In another embodiment of the present disclosure, the Trigofoenoside is present at concentration ranging from about 0.1% w/w to about 8% w/w; the Vitexin is present at concentration ranging from about 0.5% w/w to about 5% w/w; the Iso-vitexin is present at concentration ranging from about 0.5% w/w to about 7% w/w; the Vitexin-2-o-rhamnoside is present at concentration ranging from about 0.5% w/w to about 7% w/w; the Vicenin-1 is present at concentration ranging from about 0.5% w/w to about 4% w/w; and the fiber is present at concentration ranging from about 69% w/w to about 92% w/w.

In yet another embodiment of the present disclosure, the pharmaceutically acceptable excipient is selected from group comprising gum, granulating agent, binder, lubricant, disintegrating agent, sweetening agent, additive, solvent, glidant, anti-adherent, anti-static agent, anti-oxidant, surfactant, viscosity enhancer, plant cellulosic material, coloring agent, flavoring agent, coating agent, plasticizer, preservative, suspending agent, emulsifying agent and spheronization agent or any combinations thereof.

In yet another embodiment of the present disclosure, the composition is formulated into dosage forms selected from group comprising solid oral formulation, liquid oral formulation, inhalation formulation, nasal formulation, parenteral formulation, phytoceutical, nutraceutical and food stuff or any combinations thereof.

In yet another embodiment of the present disclosure, the solid oral formulation is selected from group comprising tablet, capsule, troche, lozenge, dispersible powder, dispersible granule or any combinations thereof; the liquid oral formulation is selected from group comprising aqueous or oily suspension, emulsion, drop, emulsion in hard or soft gel capsule, syrup, elixir or any combinations thereof; the parenteral formulation is selected from group comprising intravenous injection, intramuscular injection, intramuscular depot, subcutaneous injection, percutaneous injection or any combinations thereof; the inhalation formulation is selected from group comprising inhaler, dry powder inhaler, nebulizer or any combinations thereof; and the nasal formulation is selected from group comprising nasal drops, nasal sprays or a combination thereof.

In yet another embodiment of the present disclosure, the composition is administered at dose ranging from about 1 mg/kg to about 100 mg/kg of body weight of said subject, preferably ranging from about 1 mg/kg to about 40 mg/kg of body weight of said subject.

In yet another embodiment of the present disclosure, the composition is administered as a spray or inhaler at dose ranging from about 1 µg/kg to about 100 µg/kg of body weight of said subject, preferably ranging from about 1 µg/kg to about 25 µg/kg of body weight of said subject.

In still another embodiment of the present disclosure, the subject is a mammal, including human being.

The present disclosure relates to a composition comprising Trigofoenoside, Vitexin, Iso-vitexin, Vitexin-2-o-rhamnoside, Vicenin-1 and fiber, optionally along with pharmaceutically acceptable excipient(s), also referred to as the 'instant composition' throughout the specification.

In an embodiment of the present disclosure, Trigofoenoside, Vitexin, Iso-vitexin, Vitexin-2-o-rhamnoside and Vicenin-1, together constitute about 8% w/w to about 31% w/w of the composition while the fiber constitutes about 69% w/w to about 92% w/w of the composition.

In another embodiment of the present disclosure, the composition comprises about 0.1% w/w to about 8% w/w of Trigofoenoside, about 0.5% w/w to about 5% w/w of Vitexin, about 0.5% w/w to about 7% w/w of Iso-vitexin, about 0.5% w/w to about 7% w/w of Vitexin-2-o-rhamnoside, about 0.5% w/w to about 4% w/w of Vicenin-1 and about 69% w/w to about 92% w/w of fiber.

In another embodiment of the present disclosure, the pharmaceutically acceptable excipient is present at concentration ranging from about 10% w/w to about 70% w/w.

In another embodiment of the present disclosure the pharmaceutically acceptable excipient(s) is selected from group comprising gum, granulating agent, binder, lubricant, disintegrating agent, sweetening agent, additive, solvent, glidant, anti-adherent, anti-static agent, anti-oxidant, surfactant, viscosity enhancer, plant cellulosic material, coloring agent, flavoring agent, coating agent, plasticizer, preservative, suspending agent, emulsifying agent and spheronization agent or any combinations thereof.

In an embodiment of the present disclosure, the composition is obtained from a biological source material. In an exemplary embodiment, the composition is obtained from plant source, preferably from Fenugreek (*Trigonella foenum-graecum*).

In a non-limiting embodiment of the present disclosure, the composition is in the form of a plant extract, including but not limited to Fenugreek based extract.

The present disclosure provides for a simple, cost-effective and efficient method for obtaining composition/extract comprising Trigofoenoside, Vitexin, Iso-vitexin, Vitexin-2-o-rhamnoside, Vicenin-1 and Fiber. In a non-limiting embodiment, the composition/extract is obtained from Fenugreek (*Trigonella foenum-graecum*) and the method of preparing the composition/extract broadly comprises acts of flaking seeds of Fenugreek in a flaker to expose the inner core, resulting in flakes of average 2 mm in size, subjecting the flaked seeds to series of extraction steps followed by acts selected from group comprising concentrating the extract, dilution, adsorption, chromatography, elution and concentration, or any combinations thereof.

In an embodiment of the present disclosure, post flaking, the fenugreek seeds are subjected to extraction with first solvent which is an aliphatic compound. In an exemplary embodiment, the solvent is n-alkane selected from group comprising n-Hexane, n-pentane, n-heptane, preferably n-Hexane. This step is carried out at room temperature of about 25° C. to about 30° C., preferably about 25° C. to about 27° C., at time period of about 3.8 hours to about 4.2 hours, preferably about 4 hours and enables removal of lipids and oils. Post extraction with the first solvent, the extract obtained is treated with second solvent, preferably ethyl acetate. This step is carried out at temperature ranging from about 26° C. to about 30° C., preferably about 27° C. to about 29° C. and enables removal of alkaloids and other colouring impurities. This is followed by re-extraction with third solvent, preferably n-butanol in a counter current manner at temperature ranging from about 22° C. to about 27° C., preferably about 22° C. to about 25° C., at time period ranging from about 7 hours to about 9 hours, preferably about 8 hours. The extract obtained is then vacuum concentrated and dissolved in de-ionized water and the clear solution thus obtained is passed through an adsorbent resin which is regenerated and washed with solvent selected from group comprising isopropyl alcohol, ethanol and deionized water, or any combinations thereof. The outlet of the column/resin is monitored using chromatography, preferably Thin Layer Chromatography. Once the entire clear solution has passed through the adsorbent resin, the resin/column is washed with solvent selected from group comprising sodium chloride saline and water, or a combination thereof and eluted using solvent selected from group comprising ethanol and isopropyl alcohol, preferably isopropyl alcohol. The elute is then collected and concentrated to obtain the composition of the present disclosure. Excipient(s) may optionally be added to the final composition.

In another non-limiting embodiment of the present disclosure, the method of obtaining the composition comprises sequential addition and combining of Trigofoenoside, Vitexin, Iso-vitexin, Vitexin-2-o-rhamnoside, Vicenin-1 and Fiber, optionally along with pharmaceutically acceptable excipients to obtain the instant composition.

In an exemplary embodiment, Trigofoenoside, Vitexin, Iso-vitexin, Vitexin-2-o-rhamnoside, Vicenin-1 are added such that they together constitute about 8% w/w to about 31% w/w of the composition and the fiber is added such that it constitutes about 69% w/w to about 92% w/w of the composition.

In another exemplary embodiment, the method comprises combining about 0.1% w/w to about 8% w/w of Trigofoenoside, about 0.5% w/w to about 5% w/w of Vitexin, about 0.5% w/w to about 7% w/w of Iso-vitexin, about 0.5% w/w to about 7% w/w of Vitexin-2-o-rhamnoside, about 0.5% w/w to about 4% w/w of Vicenin-1 and about 69% w/w to about 92% w/w of fiber, to obtain the composition. In an alternative embodiment of the present disclosure, the composition may be obtained by chemical synthesis.

In an exemplary embodiment, the composition of the present disclosure is used to manage disease conditions such as hypoxia, Pulmonary hypertension, pulmonary fibrosis and sinusitis, or any combinations thereof.

The present disclosure further provides a method of managing disease conditions selected from group comprising hypoxia, Pulmonary hypertension, pulmonary fibrosis and sinusitis, or any combinations thereof, by administering the instant composition to a subject in need thereof.

In an embodiment of the present disclosure, the term "managing" or "management" includes preventing, treating and healing of a disease condition or disorder or ill effects or side effects. The term also encompasses maintenance of the optimum state and prevention of the further progress in the disease condition or disorder or ill effects or side effects. In another embodiment of the present disclosure, the subject is a mammal, including human beings.

In yet another embodiment of the present disclosure, the composition is formulated into dosage forms selected from group comprising solid oral formulation, liquid oral formulation, inhalation formulation, nasal formulation, parenteral formulation, phytoceutical, nutraceutical and food stuff or any combinations thereof. The solid oral formulation is selected from group comprising tablet, capsule, troche, lozenge, dispersible powder, dispersible granule or any combinations thereof; the liquid oral formulation is selected from group comprising aqueous or oily suspension, emulsion, drops, emulsion in hard or soft gel capsule, syrup, elixir or any combinations thereof; the parenteral formulation is selected from group comprising intravenous injection, intramuscular injection, intramuscular depot, subcutaneous injection, percutaneous injection or any combinations thereof; the inhalation formulation is selected from group comprising inhaler, dry powder inhaler, nebulizer or any combinations thereof; and the nasal formulation is selected from group comprising nasal drops, nasal sprays or a combination thereof.

In a non-limiting embodiment of present disclosure, administration of the composition is carried out orally.

In still another embodiment of the present disclosure, the instant composition is formulated into a suitable dosage formulation for obtaining a therapeutic effect. In an embodiment of the present disclosure, the dose of the instant composition for subjects is calculated according to the USFDA guidelines for the industry.

In an exemplary embodiment, the composition is administered at dose ranging from about 1 mg/kg to about 100 mg/kg of body weight of the subject, preferably ranging from about 1 mg/kg to about 40 mg/kg of body weight of the subject.

In another exemplary embodiment, the composition is administered as a spray or inhaler at dose ranging from about 1 µg/kg to about 100 µg/kg of body weight of the subject, preferably ranging from about 1 µg/kg to about 25 µg/kg of body weight of the subject.

The present disclosure is further elaborated with the help of the following examples. However, these examples should not be construed to limit the scope of the present disclosure.

EXAMPLES

Example 1(a)

Preparation of the Instant Composition from Fenugreek 500 g of fenugreek seeds are flaked to a thickness of about 2 mm and then extracted with about 3000 ml of n-Hexane at room temperature for about 4 hours to remove the lipids and oils. The extract is treated with about 2000 ml of ethyl acetate to remove alkaloids and other colouring impurities. These extracted fenugreek flakes are re-extracted with about 2000 ml of n-Butanol in a counter-current manner for about 8 hours. This clear n-Butanol extract is concentrated to get a solid mass weighing about 6.5 g which is then dissolved in 250 ml of de-ionized water to get a clear solution. This solution is then passed through an adsorbent resin bed containing about 25 ml of Amberlite xad-16 resin which is regenerated and washed with isopropyl alcohol followed by deionized water. The outlet of column is monitored for the absence of compounds using Thin Layer Chromatography in the following system—Chloroform (about 8 ml): methanol (about 2 ml): about 1 drop of water. Once the entire quantity is passed, the column is washed with 0.9% sodium chloride saline followed by about 250 ml of water. The column is eluted with about 250 ml of isopropyl alcohol, following which the elute is collected and concentrated to get a free-flowing pale brown powder of about 1.4 g, which is the instant composition comprising Trigofoenoside, Vitexin, Iso-vitexin, Vitexin-2-o-rhamnoside, Vicenin-1 and fiber.

Further, for validating that the powder comprises the above mentioned components, the powder is analyzed using HPLC and Gravimetry.

Figure 1A:
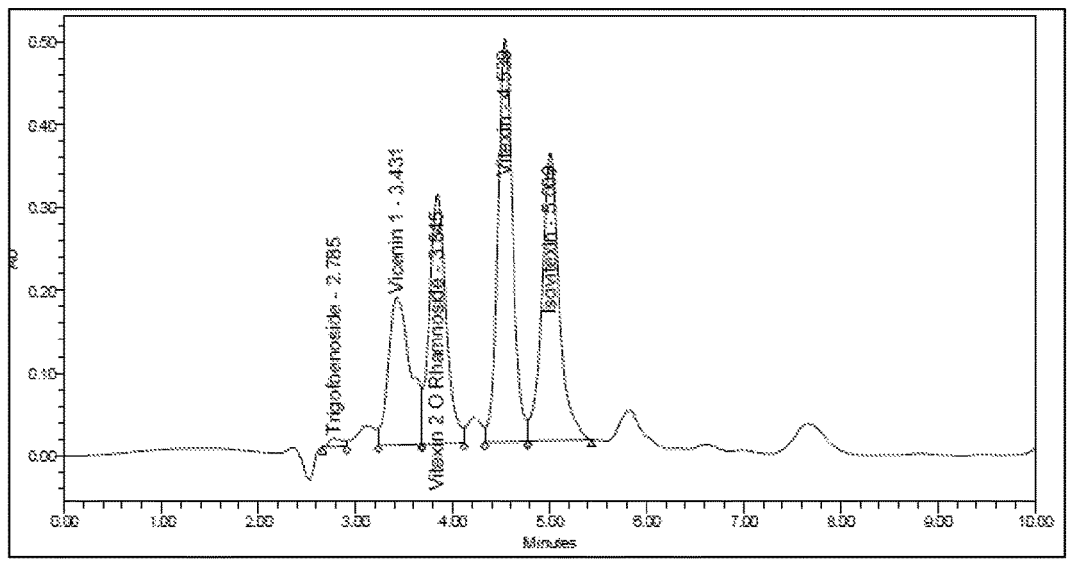

HPLC Method
Sample Name: RD # FE 691
Vial: 1:A, 1
Injection #: 1
Injection Volume: 20.00 µl
Run Time: 10:00 minutes Upon carrying out HPLC, five peaks are obtained. HPLC graph of the instant composition is shown in FIG. 1a. The peaks are found to correspond to active components, Trigofoenoside, Vitexin, Iso-vitexin, Vitexin-2-o-rhamnoside and Vicenin-1, by comparing with the HPLC graphs of standards (FIGS. 2a-2e).

The concentrations of the five components analysed using HPLC are calculated from the HPLC graph using standard protocol and are provided in Table 1 below:

TABLE 1

Concentration of Components in Instant Composition

| S. No. | Component | Concentration (%) |
|---|---|---|
| 1 | Trigofoenoside, | 4.075 |
| 2 | Vitexin, | 3.415 |
| 3 | Iso-vitexin, | 2.800 |
| 4 | Vitexin-2-o-rhamnoside | 3.369 |
| 5 | Vicenin-1 | 1.554 |

Gravimetric Analysis
Protocol

To about 1 g of the powder obtained, about 40 ml of iso propyl alcohol (IPA) is added and stirred at room temperature for about 30 minutes. The solution is filtered, post which, a clear IPA extract is obtained which is evaporated to a residue on water bath and cooled to room temperature. About 100 ml of acetone is added to the above residue and stirred for about 30 minutes at room temperature. This solution is filtered through Whatman filter paper (previously weighed). The precipitate is dried at about 100° C. for about 2 hours, following which the precipitate and filter paper are weighed again.

Calculation for Determining Concentration of Fiber:

Weight of precipitate=Weight. of filter paper with precipitate−Weight of filter paper Concentration of Soluble fiber=[(Initial weight of the sample−weight of the precipitate)/Initial weight of the sample]×100

Based on the same, the concentration of soluble fiber obtained is determined to be about 77%

Example 1(b)

Method for Preparation of the Instant Composition from Fenugreek 500 g of fenugreek seeds are flaked to a thickness of about 2 mm and then extracted with about 3000 ml of n-Heptane at room temperature for about 3.8 hours to remove the lipids and oils. The extract is treated with about 2000 ml of ethyl acetate to remove alkaloids and other colouring impurities. These extracted fenugreek flakes are re-extracted with about 2000 ml of n-Butanol in a counter-current manner for about 8 hours. This clear n-Butanol extract is concentrated to get a solid mass weighing about 6.5 g which is then dissolved in 250 ml of de-ionized water to get a clear solution. This solution is then passed through an adsorbent resin bed containing about 25 ml of Amberlite xad-16 resin which is regenerated and washed with ethanol followed by deionized water. The outlet of column is monitored for the absence of compounds using Thin Layer Chromatography in the following system—Chloroform (about 8 ml): methanol (about 2 ml): about 1 drop of water. Once the entire quantity is passed, the column is washed with 0.9% sodium chloride saline followed by about 250 ml of water. The column is eluted with about 250 ml of isopropyl alcohol, following which the elute is collected and concentrated to get a free-flowing pale brown powder of about 1.2 g, which is the instant composition comprising Trigofoenoside, Vitexin, Iso-vitexin, Vitexin-2-o-rhamnoside, Vicenin-1 and fiber.

Figure 1B:
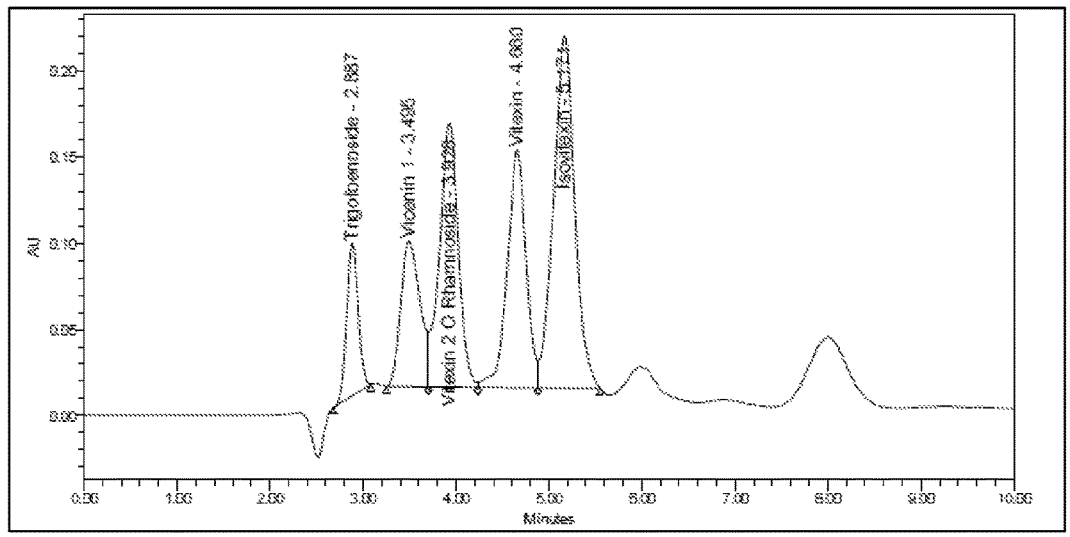
Figure 2A:
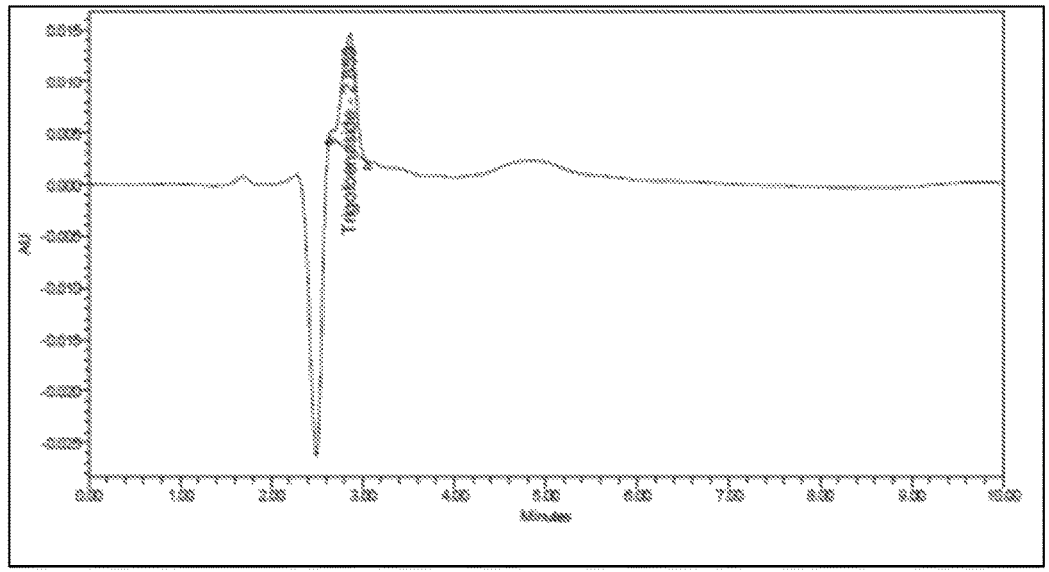
Figure 2B:
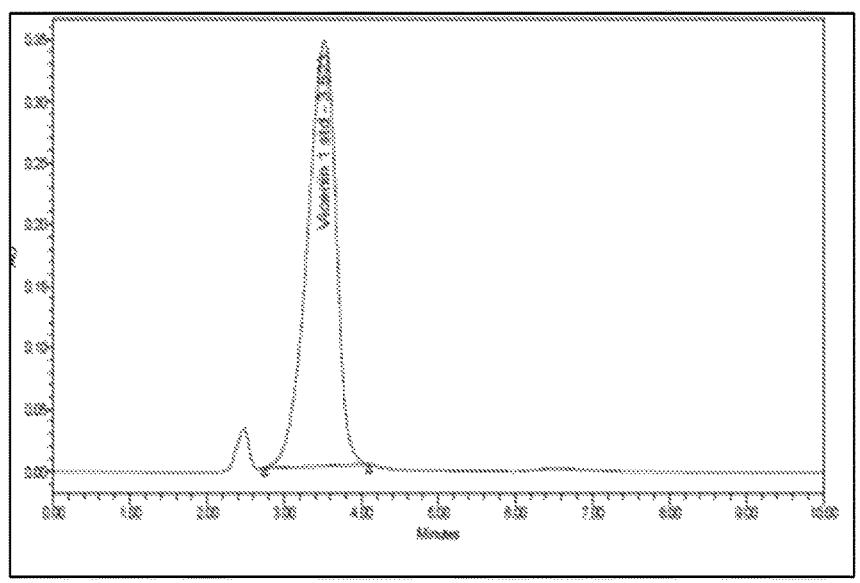
Figure 2C:
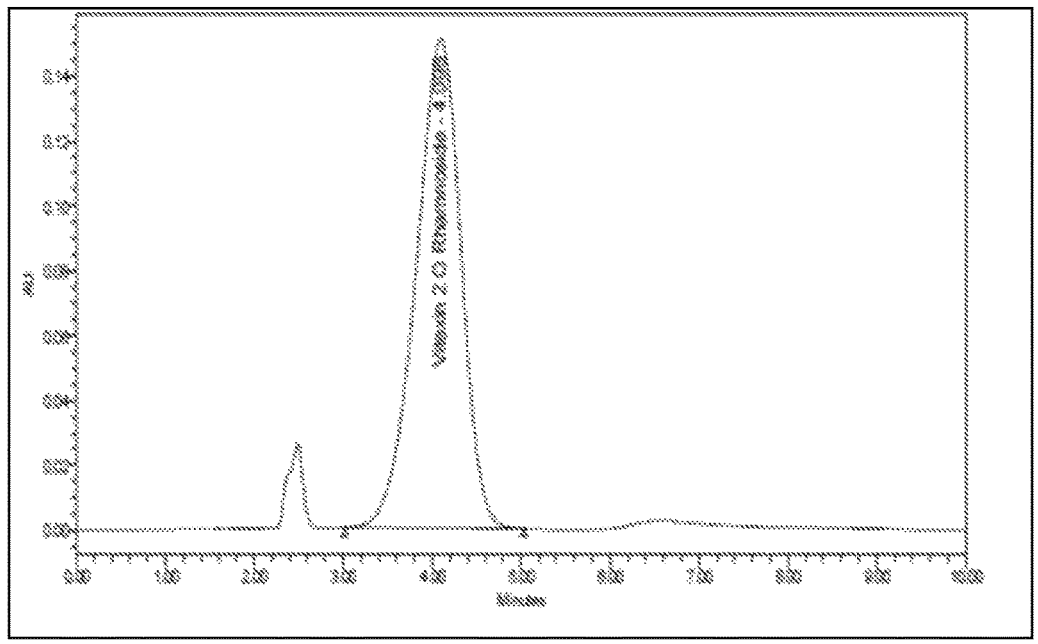
Figure 2D:
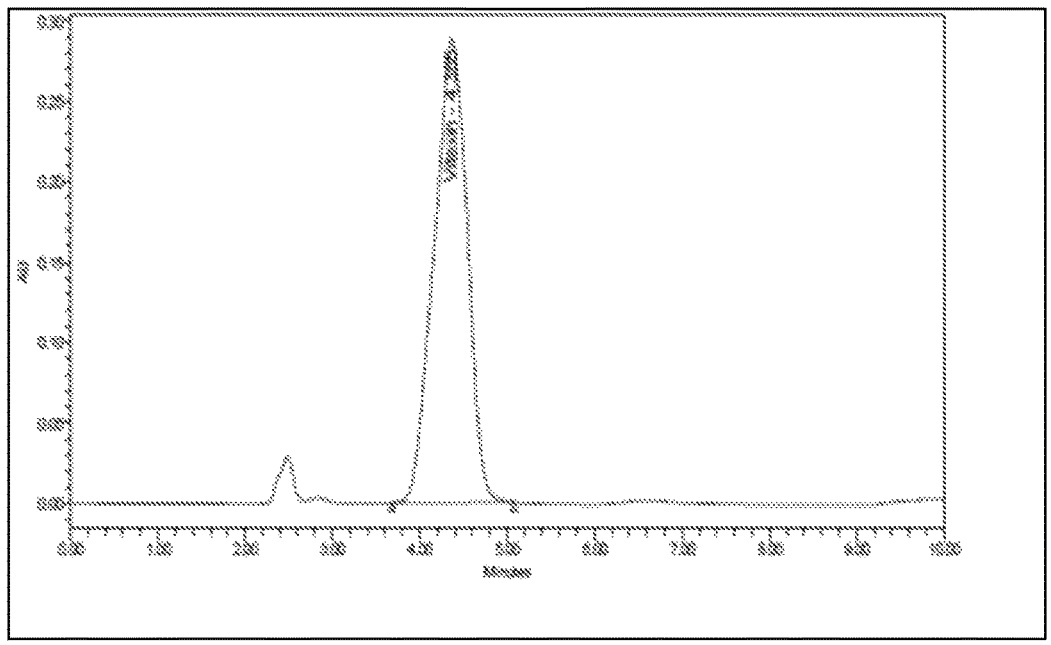
Figure 2E:
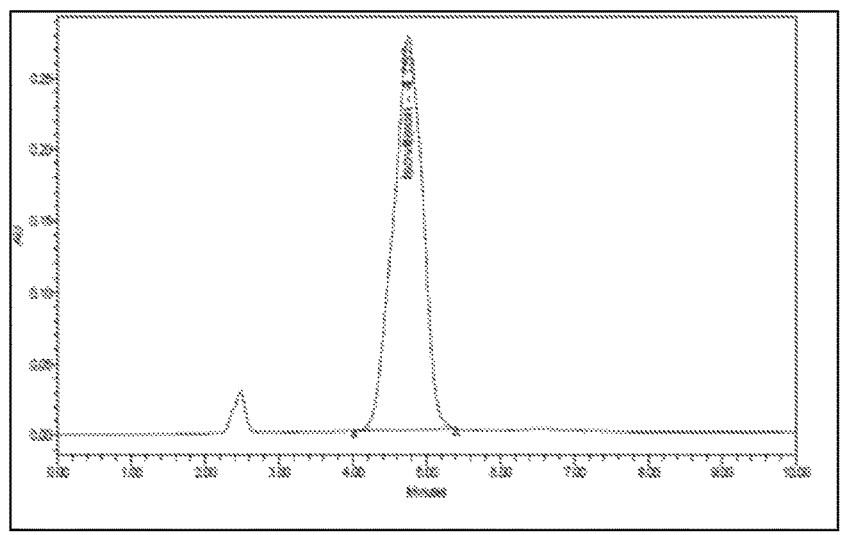

HPLC Method
Sample Name: IND 830 Plant Batch
Vial: 1:A, 7
Injection #: 1
Injection Volume: 20.00 µl
Run Time: 10:00 minutes Upon carrying out HPLC, five peaks are obtained. HPLC graph of the instant composition is shown in FIG. 1b. The peaks are found to correspond to active components, Trigofoenoside, Vitexin, Iso-vitexin, Vitexin-2-o-rhamnoside and Vicenin-1, by comparing with the HPLC graphs of standards (FIGS. 2a-2e).

The concentrations of the five components analysed using HPLC are calculated from the HPLC graph using standard protocol and are provided in Table 2 below:

TABLE 2

Concentration of Components in Instant Composition

| S. No. | Component | Concentration (%) |
|---|---|---|
| 1 | Trigofoenoside, | 3.259 |
| 2 | Vitexin, | 1.300 |
| 3 | Iso-vitexin, | 2.094 |
| 4 | Vitexin-2-o-rhamnoside | 2.022 |
| 5 | Vicenin-1 | 0.679 |

Gravimetric Analysis
Protocol

To about 1 g of the powder obtained, about 40 ml of iso propyl alcohol (IPA) is added and stirred at room temperature for about 30 minutes. The solution is filtered, post which, a clear IPA extract is obtained which is evaporated to a residue on water bath and cooled to room temperature. About 100 ml of acetone is added to the above residue and stirred for about 30 minutes at room temperature. This solution is filtered through Whatman filter paper (previously weighed). The precipitate is dried at about 100° C. for about 2 hours, following which the precipitate and filter paper are weighed again.

Calculation for Determining Concentration of Fiber:

Weight of precipitate=Weight. of filter paper with precipitate–Weight of filter paper Concentration of Soluble fiber=[(Initial weight of the sample–weight of the precipitate)/Initial weight of the sample]×100

Based on the same, the concentration of soluble fiber obtained is determined to be about 79%.

Example 2

Method for Preparation of the Instant Composition

About 0.1% w/w to about 8% w/w of Trigofoenoside, about 0.5% w/w to about 5% w/w of Vitexin, about 0.5% w/w to about 7% w/w of Iso-vitexin, about 0.5% w/w to about 7% w/w of Vitexin-2-o-rhamnoside, and about 0.5% w/w to about 4% w/w of Vicenin-1 are added sequentially and combined, following which about 69% w/w to about 92% w/w of fiber is added to the combination, optionally along with pharmaceutically acceptable excipient(s), to obtain the instant composition.

Example 3

Evaluation of the Instant Composition on Hypoxia, Pulmonary Hypertension, Pulmonary Fibrosis and Sinusitis Pulmonary Hypertension (PAH) is induced in male Sprague Dawley rats weighing about 200-220 g, by subcutaneous administration of Monocrotaline (MCT) (60 mg/kg) under anaesthesia. Animals administered with Monocrotaline (MCT) are treated with either vehicle (10 mg/kg distilled water, p.o.) or Instant composition (10 mg/kg, 20 mg/kg and 40 mg/kg, p.o.) for 28 days. The requisite parameters are evaluated on various days.

Animal Model:

Pulmonary artery hypertension (PAH) is characterized by remodelling of the pulmonary arteries with endothelial proliferation, smooth muscle hyperplasia and hypertrophy, and expansion of the adventitial matrix. An increase in pulmonary arterial pressure, right ventricular hypertrophy, and eventual cor pulmonale are the manifestations of a complex pathophysiology that composes this disease. A model that is frequently used for study of functional, structural, and molecular changes associated with right ventricular (RV) compensated hypertrophy and RV failure is treatment of rats with monocrotaline (MCT). It is a phytotoxin derived from the seeds of *Crotalaria spectabilis* and is in vivo activated by mixed function oxidases in the liver to form the reactive bifunctional cross-linking compound MCT pyrrole. MCT exhibits a selective toxic effect on pulmonary vessels without having any effect on systemic vessels since the lungs represent the first major vascular bed distal to the liver.

Example 3.1

Evaluation of the Instant Composition on Hypoxia

The instant Composition obtained in Example 1(a) is used in the following experiments.

Evaluation of Hypoxia is carried out using the following parameters:
  a. Peripheral blood oxygen content
  b. Lung function measurements
    i. Breathing rate
    ii. Enhanced pause Effect of the Instant Composition on MCT Induced Alteration in Peripheral Blood Oxygen Content (Pulse Ox) of Rats:

Pulse oximetry is particularly convenient for non-invasive continuous measurement of blood oxygen saturation. A blood-oxygen monitor displays the percentage of blood that is loaded with oxygen. More specifically, it measures what percentage of haemoglobin, the protein in blood that carries oxygen, is loaded.

Figure 3:
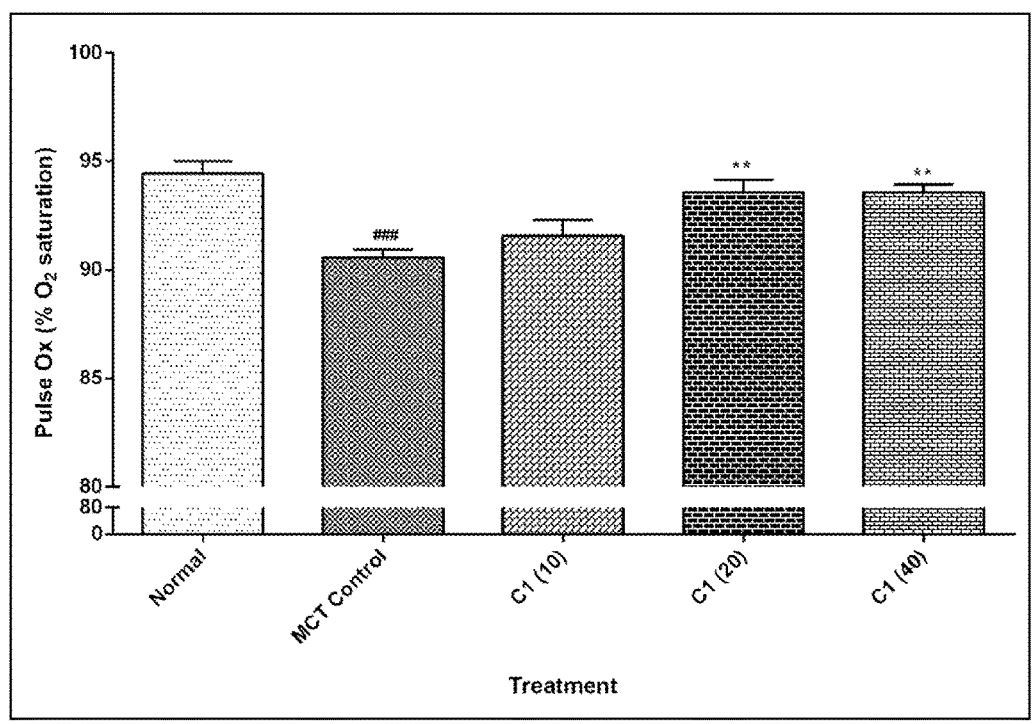
FIG. 3 is a bar graph depicting the effect of the instant composition on MCT induced alteration in peripheral blood oxygen content (pulse Ox), according to one embodiment.

Data is analyzed by One-Way ANOVA followed by Dunnett's post tests. ###$P<0.001$ as compared with normal group, and $P<0.01$, *$P<0.001$ as compared with MCT control group. The results are shown in Table 3 below and FIG. 3 (Day 28 result).

TABLE 3

Effect of the Instant Composition on MCT induced alteration in peripheral blood oxygen content (pulse Ox)

| | Normal | MCT Control | Instant Composition C1(10) (10 mg/kg) | Instant Composition C1(20) (20 mg/kg) | Instant Composition C1(40) (40 mg/kg) |
|---|---|---|---|---|---|
| Pulse Ox (% $O_2$ saturation) | 94.43 ± 0.57 | 90.57 ± 0.36[####] | 91.57 ± 0.75 | 93.57 ± 0.57** | 93.57 ± 0.36** |

As can be observed, the peripheral blood oxygen content decreases significantly (P<0.001) in MCT control group as compared to normal group on day 28. Treatment with the Instant Composition, particularly at concentrations of 20 mg/kg and 40 mg/kg produce significant increase (P<0.01) in peripheral blood oxygen content as compared to MCT control rats reaching to the normal level.

Figure 4:
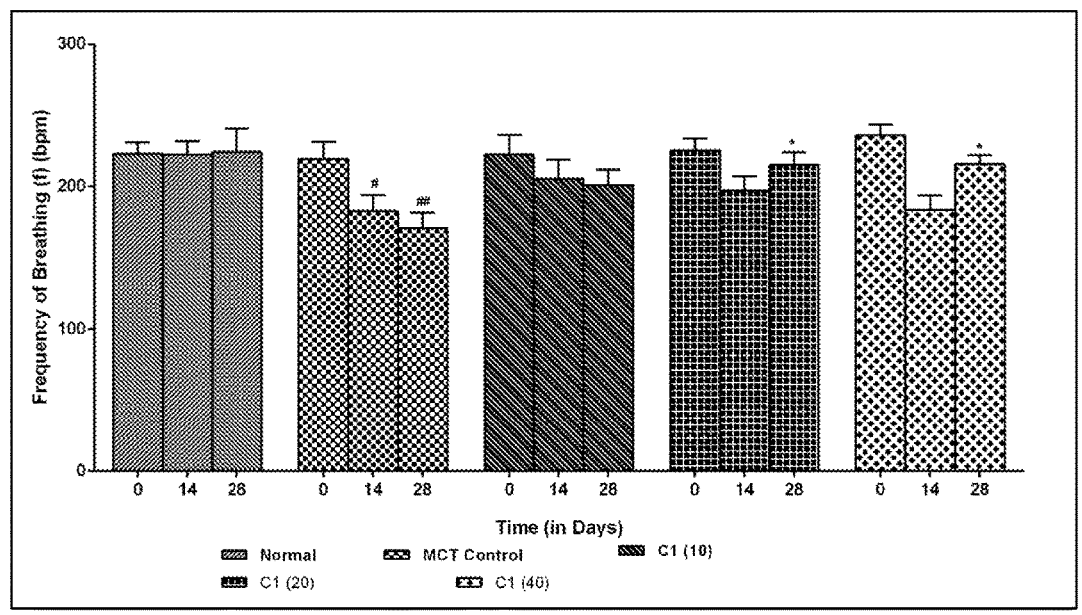
FIG. 4 is a bar graph depicting the effect of the instant composition on MCT induced alteration in frequency of breathing (f), according to one embodiment.

Effect of the Instant Composition on MCT Induced Alteration in Frequency of Breathing (f) of Rats:

Data is analyzed by Two-Way ANOVA followed by Bonferroni's post tests. [#]P<0.05, [##]P<0.01 as compared with normal group, and *P<0.05 as compared with MCT control group on respective days, and the results are shown in Table 4 below as well as in FIG. 4.

TABLE 4

Effect of the Instant Composition on MCT induced alteration in frequency of breathing (f) of rats

| Time (in days) | Normal | MCT Control | Instant Composition C1(10) (10 mg/kg) | Instant Composition C1(20) (20 mg/kg) | Instant Composition C1(40) (40 mg/kg) |
|---|---|---|---|---|---|
| 0 | 222.67 ± 8.27 | 219.11 ± 11.92 | 222.30 ± 13.59 | 224.94 ± 8.63 | 235.67 ± 8.09 |
| 14 | 222.07 ± 9.59 | 182.71 ± 11.26[#] | 205.19 ± 13.32 | 196.93 ± 10.15 | 183.33 ± 10.32 |
| 28 | 224.04 ± 16.78 | 170.37 ± 11.25[##] | 200.86 ± 10.77 | 214.93 ± 8.90* | 215.56 ± 6.05* |

It can be observed that there is no significant difference in the frequency of breathing of MCT control group as well as normal group on day 0. The frequency of breathing decreases significantly (P<0.05 and P<0.01) in the MCT control rats after 14 days and 28 days of subcutaneous MCT administration as compared to normal group. When compared with MCT control group, this frequency of breathing is significantly increased (P<0.05) in the instant composition treatment group (20 mg/kg and 40 mg/kg) after 28 days of treatment.

Effect of the Instant Composition on MCT Induced Alteration in Enhanced Pause ($P_{enh}$) of Rats:

$P_{enh}$ is a dimensionless index normally used to evaluate changes in the shape of the airflow pattern entering and leaving a whole-body flow plethysmograph as an animal breathes. The index is sensitive to changes in the distribution of area under the waveform during exhalation and increases in a nonlinear fashion as the normalized area increases near the beginning of the curve.

Figure 5:
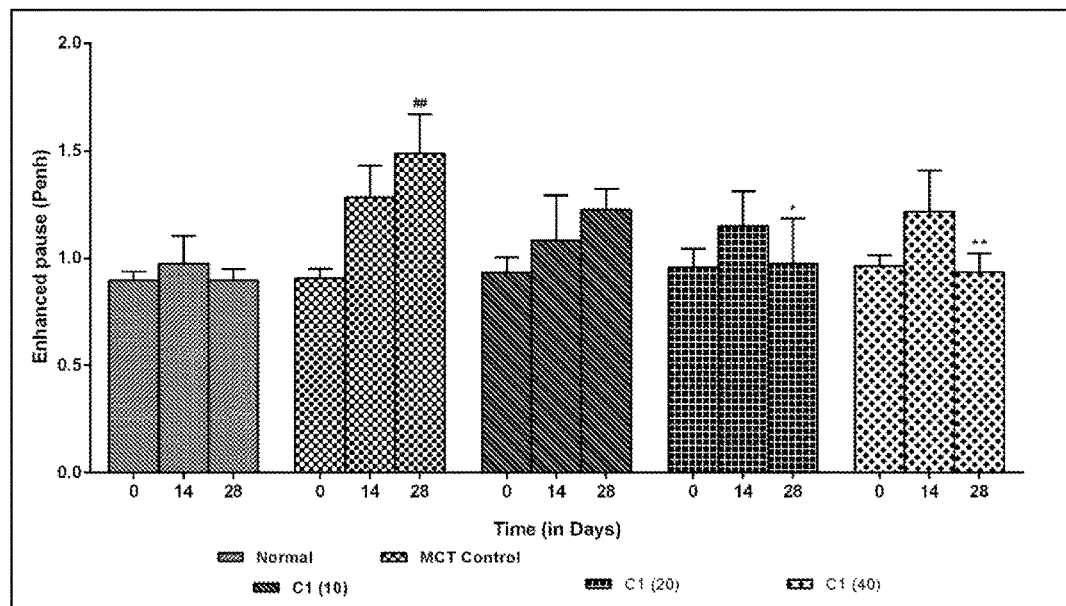
FIG. 5 is a bar graph depicting the effect of the instant composition on MCT induced alteration in enhanced pause ($P_{enh}$), according to one embodiment.

Data is analyzed by Two-Way ANOVA followed by Bonferroni's post tests. [##]P<0.01 as compared with normal group, and *P<0.05, **P<0.01 as compared with MCT control group on respective days, and the results are shown in Table 5 below as well as in FIG. 5.

TABLE 5

Effect of the Instant Composition on MCT induced alteration in enhanced pause ($P_{enh}$) of rats

| Time (in days) | Normal | MCT Control | Instant Composition C1(10) (10 mg/kg) | Instant Composition C1(20) (20 mg/kg) | Instant Composition C1(40) (40 mg/kg) |
|---|---|---|---|---|---|
| 0 | 0.89 ± 0.04 | 0.90 ± 0.04 | 0.93 ± 0.07 | 0.95 ± 0.08 | 0.96 ± 0.05 |
| 14 | 0.97 ± 0.12 | 1.28 ± 0.14 | 1.08 ± 0.21 | 1.15 ± 0.16 | 1.21 ± 0.19 |
| 28 | 0.89 ± 0.05 | 1.48 ± 0.18[##] | 1.22 ± 0.09 | 0.97 ± 0.20* | 0.93 ± 0.08** |

As can be observed, there is no significant difference in the enhanced pause of MCT control group as well as normal group and the Instant Composition (10 mg/kg, 20 mg/kg and 40 mg/kg) treated group on day 0. The enhanced pause is increased significantly (P<0.01) in the MCT control rats after 28 days of subcutaneous MCT administration as compared to normal group. When compared with MCT control group, this enhanced pause is significantly and dose dependently decreased (P<0.05 and P<0.01) in the Instant Composition (20 mg/kg and 40 mg/kg) treatment group after 28 days.

Conclusion

From the above results, it is clear that the Instant Composition effectively normalizes blood oxygen saturation resulting in restoration of percentage of haemoglobin that carries oxygen through the blood. Normalization of breathing rate is indicative of adequate oxygen supply by the Instant Composition. It also normalizes changes in the shape of the airflow pattern entering and leaving a whole-body flow in case of low oxygen levels. Thus all the above findings prove that the Instant Composition is a safe and efficacious drug for Hypoxia.

Example 3.2

Effect of the Instant Composition on Pulmonary Hypertension Using Hemodynamic Measurements The Instant Composition obtained in Example 1(a) is used in the following experiments.

Hemodynamic Measurements include many parameters such as $dP/dt_{max}$, $dP/dt_{min}$, contractility index and tau. These parameters help to elaborate on air flow pressures such as ratio of systolic pressure and diastolic pressure over time. They also elaborate on pressure fall and its analysis, through the time constant (tau) which allows a description of the course of myocardial relaxation.

Systolic performance is assessed by the contractility index of $dP/dt_{max}$ whereas diastolic dysfunction is elicited in response to increased afterload. Diastole is evaluated with the time constant of iso volumetric relaxation (tau) and the end diastolic pressure-diameter relation (EDPDR)—the former evaluates active relaxation while the latter is an in vivo estimate of myocardial stiffness. The dynamic process of myocardial relaxation goes on from the ejection phase to the early filling period.

Effect of the Instant Composition on MCT Induced Alteration in Right Ventricular $dP/Dt_{max}$ and Right Ventricular $dP/Dt_{min}$ of Rats:

Data is analyzed by One-Way ANOVA followed by Dunnett's post tests. [##]P<0.01, [###]P<0.001 as compared with normal group, and *P<0.05, P<0.01, *P<0.001 as compared with MCT control group on respective days. The results are shown in Table 6 below and in FIGS. 6a and 6b.

TABLE 6

Effect of the Instant Composition on MCT induced alteration in right ventricular $dP/dt_{max}$ and right ventricular $dP/dt_{min}$ of rats

| | Normal | MCT Control | Instant Composition C1(10) (10 mg/kg) | Instant Composition C1(20) (20 mg/kg) | Instant Composition C1(40) (40 mg/kg) |
|---|---|---|---|---|---|
| $dP/dt_{max}$ (mm Hg) | 982.3 ± 46.15 | 1376.00 ± 94.80## | 1254.00 ± 66.92 | 1090.00 ± 55.16* | 1042.00 + 65.86** |
| $dP/dt_{min}$ (mm Hg) | −746.6 ± 76.15 | −1356.00 ± 66.02#### | −1105.00 ± 39.62* | −1041.00 ± 33.43** | −1021.00 ± 46.38*** |

As can be observed, there is a significant increase (P<0.01 and P<0.001) in the $dP/dt_{max}$ as well as $dP/dt_{min}$ in the MCT control group as compared to the normal group after 28 days of subcutaneous administration of MCT. Administration of the instant composition (20 mg/kg and 40 mg/kg) significantly and dose dependently decreases (P<0.05 and P<0.01) the $dP/dt_{max}$ as compared to MCT control group whereas the administration of instant composition at all three dosages significantly and dose dependently decreases (P<0.05, P<0.01 and P<0.001, reps.) $dP/dt_{min}$ as compared to MCT control group.

Effect of the Instant Composition on MCT Induced Alteration in Contractility Index and Tau of Rats:

Data is analyzed by One-Way ANOVA followed by Dunnett's post tests. ####P<0.001 as compared with normal group, and *P<0.05, ***P<0.001 as compared with MCT control group on day 28. Results are shown in Table 7 below and FIGS. 7a and 7b.

TABLE 7

Effect of the Instant Composition on MCT induced alteration in contractility index and tau of rats

| | Normal | MCT Control | Instant Composition C1(10) (10 mg/ml) | Instant Composition C1(20) (20 mg/ml) | Instant Composition C1(40) (40 mg/ml) |
|---|---|---|---|---|---|
| Contractility index | 17.71 ± 0.91 | 8.28 ± 0.77#### | 9.28 ± 0.42 | 11.57 ± 0.52* | 13.71 ± 0.71*** |
| Tau (ms) | 14.71 ± 1.12 | 26.14 ± 1.10#### | 25.00 ± 0.97 | 21.29 ± 0.86* | 18.57 ± 0.89*** |

As can be observed, there is significant decrease (P<0.001) in the contractility index and significant increase (P<0.001) in tau in the MCT control group as compared to normal group. Administration of the Instant Composition (20 mg/kg and 40 mg/kg) significantly and dose dependently normalizes (P<0.05 and P<0.001) the contractility index as compared to MCT control group whereas the Instant Composition (20 mg/kg and 40 mg/kg) treatment on day 28 produces significant and dose dependent restoration (P<0.05 and P<0.001) in tau as compared to MCT control group.

Conclusion: The Instant Composition effectively normalizes end systolic and diastolic pressures and helps to restore contractility indices and tau showing its highly significant activity in pulmonary hypertension.

Example 3.3

Evaluation of the Instant Composition in Bleomycin-Induced Pulmonary Fibrosis

The Instant Composition obtained in Example 1(b) is used in the following experiments. Evaluation of the instant composition in bleomycin induced pulmonary fibrosis [PF] is carried out using the following parameters:

a. Lung function measurements
  i. Inspiratory time
  ii. Expiratory time
  iii. Enhanced Pause ($P_{enh}$)
b. Peripheral blood oxygen content Protocol:

PF is induced in male Sprague Dawley rats (180-220 gm) by intratracheal administration of Bleomycin (BLM) (6 IU/kg) under ketamine anaesthesia. Animals administered with Bleomycin are treated with either vehicle (10 mg/kg distilled water, p.o.) or Instant Composition (10 mg/kg, 20 mg/kg and 40 mg/kg, p.o.) for 28 days. Sham group comprise animals subjected to intratracheal administration of Vehicle (10 mg/kg distilled water, p.o.) under ketamine anaesthesia. The requisite parameters are evaluated on various days. The altered levels of lung function test and haematology are found to be significantly (P<0.01 and P<0.001) restored by the Instant Composition (20 mg/kg and 40 mg/kg, p.o.) treatment.

Animal Model:

The bleomycin-rodent paradigm of lung fibrosis is an established and widely used surrogate model of human lung fibrosis. One of the widely accepted mechanisms for bleomycin-induced lung injury is its ability to generate ROS. Bleomycin is known to bind to DNA/Fe2+ and form a complex. This DNA/Fe2+/bleomycin complex undergoes redox cycling and generates ROS such as superoxide and hydroxy radicals resulting in initiation of fibrosis.

Effect of the Instant Composition on Bleomycin Induced Alteration in Inspiratory Time ($T_1$) of Rats:

Data is analyzed by Two-Way ANOVA followed by Bonferroni's post tests ##P<0.01, ###P<0.001 as compared with normal group, $^{\$\$}$P<0.01, $^{\$\$\$}$P<0.001 as compared with sham group, and *P<0.05, P<0.01, *P<0.001 as compared with BLM control group on respective days. Results are shown in Table 8 below and in FIG. 8.

TABLE 8

Effect of the Instant Composition on bleomycin induced alteration in inspiratory time ($T_i$) of rats

| Time (Days) | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| 0 | 165.89 ± 14.77 | 152.02 ± 6.59 | 167.04 ± 8.98 | 130.65 ± 7.30 | 149.60 ± 9.69 | 137.16 ± 11.42 |
| 7 | 157.52 ± 16.55 | 166.34 ± 15.32 | 243.87 ± 11.30[##,$$] | 238.76 ± 14.36 | 231.27 ± 27.47 | 226.60 ± 21.74 |
| 14 | 168.70 ± 16.85 | 185.31 ± 13.52 | 277.20 ± 33.03[##,$$$] | 243.56 ± 28.10 | 220.63 ± 30.96 | 278.12 ± 11.08 |
| 21 | 161.75 ± 5.49 | 166.92 ± 7.63 | 302.64 ± 22.99[###,$$$] | 265.76 ± 7.34 | 234.43 ± 16.95 | 257.66 ± 17.99* |
| 28 | 161.35 ± 12.37 | 169.21 ± 9.59 | 310.38 ± 24.17[###,$$$] | 241.26 ± 20.53** | 220.75 ± 6.74** | 220.87 ± 8.09** |

As can be observed, there is no significant difference in the inspiratory time of BLM control group as compared to normal and sham group on day 0. Intratracheal instillation of BLM significantly increases (P<0.001) inspiratory time of BLM control rats as compared to normal and sham group from day 7 onwards. The day 28 treatment with the Instant Composition (10 mg/kg, 20 mg/kg and 40 mg/kg) significantly decreases (P<0.01) inspiratory time as compared to BLM control rats on day 28.

Effect of the Instant Composition on Bleomycin Induced Alteration in Expiratory Time ($T_e$) of Rats:

Data is analyzed by Two-Way ANOVA followed by Bonferroni's post tests [###]P<0.001 as compared with normal group, [$$$]P<0.001 as compared with sham group, and *P<0.05, P<0.01, *P<0.001 as compared with BLM control group on respective days. Results are shown in Table 9 below and in FIG. 9.

TABLE 9

Effect of the Instant Composition on bleomycin induced alteration in expiratory time ($T_e$) of rats

| Time (Days) | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| 0 | 202.57 ± 8.37 | 211.18 ± 12.50 | 242.41 ± 21.77 | 219.70 ± 16.18 | 199.82 ± 14.83 | 204.33 ± 28.00 |
| 7 | 219.74 ± 21.55 | 223.35 ± 18.16 | 95.17 ± 15.14[###,$$$] | 89.27 ± 6.75 | 104.56 ± 19.25 | 105.34 ± 10.25 |
| 14 | 188.33 ± 22.88 | 213.13 ± 5.44 | 95.10 ± 9.77[###,$$$] | 112.00 ± 11.25 | 123.26 ± 37.88 | 115.38 ± 7.21 |
| 21 | 198.96 ± 15.80 | 227.40 ± 18.94 | 62.87 ± 13.15[###,$$$] | 122.97 ± 18.00* | 127.23 ± 15.92* | 143.64 ± 17.06** |
| 28 | 203.94 ± 6.11 | 195.54 ± 10.60 | 62.42 ± 10.09[###,$$$] | 142.87 ± 15.50** | 132.85 ± 17.11* | 170.43 ± 12.19*** |

As can be observed, Expiratory time does not differ significantly in the BLM control group as well as in normal and sham group on day 0. However, there is significant decrease (P<0.001) in the expiratory time of BLM control rats after 7 days of intratracheal BLM instillation as compared to normal and sham group. This decreased expiratory time is significantly increased (P<0.05, P<0.01 and P<0.001) on the day 28 treatment with the Instant Composition (10, 20 and 40 mg/kg) as compared to BLM control rats.

Effect of the Instant Composition on Bleomycin Induced Alteration in Enhanced Pause ($P_{enh}$) of Rats:

Data is analyzed by Two-Way ANOVA followed by Bonferroni's post tests [###]P<0.001 as compared with normal group, [$$$]P<0.001 as compared with sham group, and ***P<0.001 as compared with BLM control group on respective days. Results are shown in Table 10 below and in FIG. 10.

TABLE 10

Effect of the Instant Composition on bleomycin induced alteration in enhanced pause ($P_{enh}$) of rats

| Time (Days) | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| 0 | 0.81 ± 0.04 | 0.80 ± 0.04 | 0.97 ± 0.11 | 0.82 ± 0.07 | 0.77 ± 0.04 | 0.75 ± 0.04 |
| 7 | 1.0 ± 0.19 | 1.03 ± 0.18 | 1.28 ± 0.11 | 1.15 ± 0.15 | 1.00 ± 0.19 | 1.42 ± 0.08 |

TABLE 10-continued

Effect of the Instant Composition on bleomycin induced alteration in enhanced pause ($P_{enh}$) of rats

| Time (Days) | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| 14 | 0.93 ± 0.16 | 0.88 ± 0.07 | 1.36 ± 0.12 | 1.38 ± 0.22 | 1.42 ± 0.03 | 1.09 ± 0.19 |
| 21 | 1.02 ± 0.14 | 0.85 ± 0.09 | 1.80 ± 0.25[###,$$$] | 1.97 ± 0.11 | 1.46 ± 0.29 | 1.41 ± 0.14 |
| 28 | 1.04 ± 0.05 | 1.15 ± 0.04 | 2.71 ± 0.19[###,$$$] | 1.82 ± 0.22*** | 1.74 ± 0.04*** | 1.64 ± 0.10*** |

As can be observed, there is no significant difference in the enhanced pause of BLM control group as well as normal and sham group on day 0, 7 and 14. The enhanced pause is increased significantly (P<0.001) in the BLM control rats after 21 days of intratracheal BLM instillation as compared to normal and sham group. When compared with BLM control group, this enhanced pause is significantly normalized (P<0.001) in the Instant Composition (10 mg/kg, 20 mg/kg and 40 mg/kg) after 28 days.

Effect of the Instant Composition on Bleomycin Induced Alteration in Peripheral Blood Oxygen Content (Pulse Ox) of Rats:

Data is analyzed by Two-Way ANOVA followed by Bonferroni's post tests [#]P<0.05, [####]P<0.001 as compared with normal group, [$]P<0.05, [$$$]P<0.001 as compared with sham group, and *P<0.05, P<0.01, *P<0.001 as compared with BLM control group on respective days. Results are tabulated in Table 11 below and in FIG. 11.

TABLE 11

Effect of the Instant Composition on bleomycin induced alteration in peripheral blood oxygen content (pulse Ox) of rats

| Time (Days) | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| 14 | 95.75 ± 0.47 | 95.25 ± 0.62 | 91.50 ± 0.64[#,$] | 92.50 ± 1.32 | 94.25 ± 0.47 | 92.00 ± 1.35 |
| 28 | 96.00 ± 0.40 | 95.00 ± 0.70 | 87.75 ± 1.31[###,$$$] | 92.00 ± 1.47* | 93.00 ± 1.08** | 92.75 ± 1.10** |

As can be observed, the peripheral blood oxygen content is decreased significantly (P<0.05 and P<0.001) in BLM control group as compared to normal and sham group on days 14 and 28 respectively. Treatment with the Instant Composition (10 mg/kg, 20 mg/kg and 40 mg/kg) does not produce any significant increase in peripheral blood oxygen content on day 14 as compared to BLM control rats. However, day 28 administration of the Instant Composition (10 mg/kg, 20 mg/kg and 40 mg/kg) significantly and dose dependently inhibits (P<0.05, P<0.01 and P<0.01) and restores BLM induced decrease in peripheral blood oxygen content as compared to BLM control rats on day 28.

Conclusion: Restoration of lung function tests such as inspiratory time, expiratory time and normalization of blood oxygen content and enhanced pause by the instant composition proves its efficacy in treating pulmonary fibrosis.

Example 3.4

Evaluation of the Instant Composition in Bleomycin-Induced Sinusitis

The Instant Composition obtained in Example 1(b) is used in the following experiments.

Evaluation of the Instant Composition in bleomycin induced pulmonary fibrosis is carried out using the following parameters:

a. RT-PCR analysis of genes in lung
  i. Muc5ac
  ii. NF-kB

Effect of the Instant Composition on Bleomycin Induced Alteration in Muc5ac m-RNA Expression in Lung of Rats:

Muc5ac is considered to be a major mucin secreted from the goblet cells of the surface epithelium. Mucus overproduction represents a component of mucociliary malfunction in respiratory disorders and Muc5ac is prominently expressed by the airway epithelium in these disorders. Oxidative stress, generated in response to bleomycin, is shown to augment Muc5ac production in bronchial epithelial cells, a process that may involve an activation of the epidermal growth factor receptor. Here, in the present investigation, bleomycin augments lung mRNA of Muc5ac and increases the mucus-forming cells of the airway epithelial layer. The Instant Composition is found to dose-dependently reduce bleomycin induced lung Muc5ac formation and epithelial mucus forming cells.

Data is analyzed by One-Way ANOVA followed by Dunnett's post tests [###]P<0.001 as compared with normal group, [$$$]P<0.001 as compared with sham group, and *P<0.05, ***P<0.001 as compared with BLM control group on day 28. Results are tabulated in Table 12 below and in FIG. 12.

TABLE 12

Effect of the Instant Composition on bleomycin induced alteration in Muc5ac in-RNA expression in lung of rats

|  | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| Muc 5ac/β-actin | 0.36 ± 0.04 | 0.48 ± 0.09 | 2.17 ± 0.21###,$$$ | 1.41 ± 0.13* | 1.04 ± 0.17*** | 0.63 ± 0.08*** |

As can be observed, Muc5ac m-RNA expression is significantly up-regulated ($P<0.001$) in the BLM control rats as compared to normal and sham group on day 28. The day 28 treatment with the Instant Composition (10 mg/kg, 20 mg/kg and 40 mg/kg) significantly and dose dependently down-regulates ($P<0.05$, $P<0.001$ and $P<0.001$) Muc5ac m-RNA in lungs as compared to BLM control rats.

Effect of the Instant Composition on Bleomycin Induced Alteration in NF-kB m-RNA Expression in Lung of Rats:

Another target for ROS generated by bleomycin is the activation of NF-kB, a transcription factor that regulates many cytokine genes, including those examined in this study, TNF-α, IL-1β, IL-6 and IL-8. TNF-α and IL-1β may in turn also activate NF-kB. Bleomycin activates the NF-κB activity in lungs, suggesting that pulmonary epithelial cells secrete NF-κB p65 (Chita et al., 2013). In the present study, the Instant Composition treatment is found to exert its effects via its antioxidant potential that inhibit oxidant induced NF-κB activation, thereby exerting the anti-fibrotic effect in the bleomycin model of pulmonary fibrosis.

Data is analyzed by One-Way ANOVA followed by Dunnett's post tests ##$P<0.01$, ###$P<0.001$ as compared with normal group, $$$P<0.01$, $$$$P<0.001$ as compared with sham group, and *$P<0.05$, ***$P<0.001$ as compared with BLM control group on day 28. Results are shown in Table 13 below and in FIG. 13.

TABLE 13

Effect of the Instant Composition on bleomycin induced alteration in NF-kB in-RNA expression in lung of rats

|  | Normal | Sham | BLM Control | Instant Composition C1(10) (10 mg/kg) | Instant Composition C1(20) (20 mg/kg) | Instant Composition C1(40) (40 mg/kg) |
|---|---|---|---|---|---|---|
| NF-kB/β-actin | 1.04 ± 0.65 | 0.67 ± 0.12 | 2.99 ± 0.21###,$$$ | 1.72 ± 0.14* | 0.95 ± 0.28*** | 0.97 ± 0.16*** |

As can be observed, there is significant up-regulation ($P<0.001$ and $P<0.01$) in the lung NF-kB m-RNA expression of BLM control group as compared to normal and sham group on day 28. However, treatment with the Instant Composition (10 mg/kg, 20 mg/kg and 40 mg/kg) significantly and down-regulates ($P<0.05$, $P<0.001$ and $P<0.001$) BLM induced up-regulated lung NF-kB m-RNA expression as compared to BLM control rats.

Conclusion: The mucus forming genes (Muc5ac, NF-kB) activate sinusitis in airway pathways of the upper respiratory tract. The dose dependent down-regulation of these genes shows efficacy of the Instant Composition in treating sinusitis.

Thus, the examples of the present disclosure show the efficacy of the Instant Composition in treating disease conditions such as Hypoxia, pulmonary hypertension, pulmonary fibrosis and sinusitis.

Additional embodiments and features of the present disclosure is apparent to one of ordinary skill in art based on the description provided herein. The embodiments herein provide various features and advantageous details thereof in the description. Descriptions of well-known/conventional methods and techniques are omitted so as to not unnecessarily obscure the embodiments herein. The foregoing description of the specific embodiments fully reveals the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein. Throughout this specification, the word "comprise", or variations such as "comprises" or "comprising" wherever used, will be understood to imply the inclusion of a stated element, integer or step, or group of elements, integers or steps, but not the exclusion of any other element, integer or step, or group of elements, integers or steps. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The use of the expression "at least" or "at least one" suggests the use of one or more elements or ingredients or quantities, as the use may be in the embodiment of the disclosure to achieve one or more of the desired objects or results. Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application. While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

We claim:

1. A composition consisting of Trigofoenoside, Vitexin, Iso-vitexin, Vitexin-2-o-rhamnoside, Vicenin-1 and fiber, optionally along with a pharmaceutically acceptable excipient.

2. The composition as claimed in claim 1, wherein the Trigofoenoside, the Vitexin, the Iso-vitexin, the Vitexin-2-o-rhamnoside and the Vicenin-1, together have a concentration ranging from about 8% w/w to about 31% w/w; and wherein the fiber is present at concentration ranging from about 69% w/w to about 92% w/w.

3. The composition as claimed in claim 1, wherein the Trigofoenoside is present at a concentration ranging from about 0.1% w/w to about 8% w/w; wherein the Vitexin is present at concentration ranging from about 0.5% w/w to about 5% w/w; wherein the Iso-vitexin is present at concentration ranging from about 0.5% w/w to about 7% w/w; wherein the Vitexin-2-o-rhamnoside is present at concentration ranging from about 0.5% w/w to about 7% w/w; wherein the Vicenin-1 is present at concentration ranging from about 0.5% w/w to about 4% w/w; and wherein the fiber is present at concentration ranging from about 69% w/w to about 92% w/w.

4. The composition as claimed in claim 1, wherein the pharmaceutically acceptable excipient is selected from group consisting of gum, granulating agent, binder, lubricant, disintegrating agent, sweetening agent, additive, solvent, glidant, anti-adherent, anti-static agent, anti-oxidant, surfactant, viscosity enhancer, plant cellulosic material, coloring agent, flavoring agent, coating agent, plasticizer, preservative, suspending agent, emulsifying agent, and spheronization agent, or any combinations thereof.

5. A method for obtaining the composition as claimed in claim 1, said method consisting of:
    a) extracting flaked fenugreek seeds with a first solvent to obtain a first extract;
    b) treating the first extract with a second solvent to obtain a second extract;
    c) re-extracting the second extract with a third solvent to obtain a clear extract;
    d) concentrating the clear extract to obtain a solid mass;
    e) dissolving the solid mass in an aqueous solvent to obtain a clear solution;
    f) regenerating and washing an adsorbent with a solvent to obtain a regenerated and washed adsorbent;
    g) passing the clear solution through the regenerated and washed adsorbent, re-washing the adsorbent with a solvent and eluting with an alcoholic solvent to obtain an elute; and
    h) concentrating the elute and optionally adding a pharmaceutically acceptable excipient to obtain the composition.

6. The method as claimed in claim 5, wherein the extracting with the first solvent is carried out at temperature ranging from about 25° C. to about 30° C., at time period of about 3.8 hours to about 4.2 hours; and wherein said first solvent is an aliphatic compound selected from the group consisting of n-Hexane, n-Pentane and n-Heptane.

7. The method as claimed in claim 5, wherein the treating with the second solvent is carried out at temperature ranging from about 26° C. to about 30° C.; and wherein said second solvent is ethyl acetate.

8. The method as claimed in claim 5, wherein the extracting with the third solvent is carried out in counter-current manner at temperature ranging from about 22° C. to about 27° C., at time period ranging from about 7 hours to about 9 hours; and wherein said third solvent is n-Butanol.

9. The method as claimed in claim 5, wherein the concentrating is carried out by vacuum concentration.

10. The method as claimed in claim 5, wherein said aqueous solvent is deionized water; wherein said adsorbent is a resin bed; wherein the solvent for washing the adsorbent is selected from the group consisting of isopropyl alcohol, ethanol and deionized water, or any combinations thereof; wherein the solvent for re-washing the adsorbent is selected from the group consisting of sodium chloride saline and water, or a combination thereof; and wherein said alcoholic solvent is selected from group comprising ethanol and isopropyl alcohol.

11. A method of treating a disease selected from group consisting of hypoxia, pulmonary hypertension, pulmonary fibrosis and sinusitis, or any combinations thereof, said method comprising administering a composition consisting of Trigofoenoside, Vitexin, Iso-vitexin, Vitexin-2-o-rhamnoside, Vicenin-1 and fiber, optionally along with a pharmaceutically acceptable excipient to a subject in need thereof.

12. The method as claimed in claim 11, wherein the Trigofoenoside, the Vitexin, the Iso-vitexin, the Vitexin-2-o-rhamnoside and the Vicenin-1, together have a concentration ranging from about 8% w/w to about 31% w/w; and wherein the
fiber is present at concentration ranging from about 69% w/w to about 92% w/w.

13. The method as claimed in claim 11, wherein the Trigofoenoside is present at concentration ranging from about 0.1% w/w to about 8% w/w; wherein the Vitexin is present at concentration ranging from about 0.5% w/w to about 5% w/w; wherein the Iso-vitexin is present at concentration ranging from about 0.5% w/w to about 7% w/w; wherein the Vitexin-2-o-rhamnoside is present at concentration ranging from about 0.5% w/w to about 7% w/w; wherein the Vicenin-1 is present at concentration ranging from about 0.5% w/w to about 4% w/w; and wherein the fiber is present at concentration ranging from about 69% w/w to about 92% w/w.

14. The method as claimed in claim 11, wherein the pharmaceutically acceptable excipient is selected from the group consisting of gum, granulating agent, binder, lubricant, disintegrating agent, sweetening agent, additive, solvent, glidant, anti-adherent, anti-static agent, anti-oxidant, surfactant, viscosity enhancer, plant cellulosic material, coloring agent, flavoring agent, coating agent, plasticizer, preservative, suspending agent, emulsifying agent, and spheronization agent, or any combinations thereof.

15. The method as claimed in claim 11, wherein the composition is formulated into a dosage form selected from the group consisting of a solid oral formulation, a liquid oral formulation, an inhalation formulation, a nasal formulation, a parenteral formulation, a phytoceutical, a nutraceutical, and a food stuff, or any combinations thereof.

16. The method as claimed in claim 15, wherein the solid oral formulation is selected from the group consisting of a tablet, a capsule, a troche, a lozenge, a dispersible powder, a dispersible granule, or any combinations thereof; wherein the liquid oral formulation is selected from the group consisting of an aqueous or oily suspension, an emulsion, a drop, an emulsion in hard or soft gel capsule, a syrup, an elixir, or any combinations thereof; wherein the parenteral formulation is selected from the group consisting of an intravenous injection, an intramuscular injection, an intramuscular depot, a subcutaneous injection, a percutaneous injection, or any combinations thereof; wherein the inhalation formulation is selected from the group consisting of an inhaler, a dry powder inhaler, a nebulizer, or any combinations thereof; and wherein the nasal formulation is selected from the group consisting of nasal drops, nasal sprays, or a combination thereof.

17. The method as claimed in claim 11, wherein the composition is administered at a dose ranging from about 1 mg/kg to about 100 mg/kg of body weight of said subject.

18. The method as claimed in claim 11, wherein the composition is administered as a spray or inhaler at a dose ranging from about 1 µg/kg to about 100 µg/kg of body weight of said subject.

19. The method as claimed in claim 11, wherein the subject is a mammal.

* * * * *